US005793485A

United States Patent [19]
Gourley

[11] Patent Number: 5,793,485
[45] Date of Patent: Aug. 11, 1998

[54] RESONANT-CAVITY APPARATUS FOR CYTOMETRY OR PARTICLE ANALYSIS

[75] Inventor: Paul L. Gourley, Albuquerque, N. Mex.

[73] Assignee: Sandia Corporation, Albuquerque, N. Mex.

[21] Appl. No.: 782,039

[22] Filed: Jan. 13, 1997

Related U.S. Application Data

[63] Continuation-in-part of Ser. No. 407,345, Mar. 20, 1995, Pat. No. 5,608,519.

[51] Int. Cl.⁶ .................................................... G01J 3/30
[52] U.S. Cl. .......................... 356/318; 356/417; 356/338; 356/339
[58] Field of Search .............................. 356/318, 417, 356/338, 339, 246, 471; 250/461.2, 458.1, 459.1

[56] References Cited

U.S. PATENT DOCUMENTS

| | | | |
|---|---|---|---|
| 3,916,197 | 10/1975 | Fulwyler | 250/361 |
| 4,243,318 | 1/1981 | Stohr | 356/39 |
| 4,765,737 | 8/1988 | Harris | 356/336 |
| 4,947,223 | 8/1990 | Biefeld | 357/30 |
| 5,021,661 | 6/1991 | Masutani | 356/318 |
| 5,100,627 | 3/1992 | Buican | 422/108 |
| 5,135,304 | 8/1992 | Miles | 356/301 |
| 5,138,170 | 8/1992 | Noguchi | 250/461.2 |
| 5,158,889 | 10/1992 | Hirako | 435/289 |
| 5,245,466 | 9/1993 | Burns | 359/296 |
| 5,296,963 | 3/1994 | Murahami | 359/389 |
| 5,322,799 | 6/1994 | Miller | 436/165 |
| 5,360,739 | 11/1994 | Fan | 436/63 |
| 5,512,492 | 4/1996 | Herron | 356/318 X |
| 5,583,634 | 12/1996 | Andre et al. | 356/318 |

OTHER PUBLICATIONS

Leon Weiss, ed., *Histology*, 5th edition, chapter 11, pp. 447–473, (Elsevier Biomedical, 1983).

A. Ashkin, J. M. Dziedzic, and T. Yamane, "Optical Trapping and Manipulation of Single Cells Using Infrared Laser Beams," *Nature*, vol. 330, pp. 769–771, Dec. 1987.

J. K. Foskett and S. Grinstein, eds., *Noninvasive Techniques in Cell Biology*, chapter 15, pp. 375–402, (John Wiley, 1990).

Y. Kikuchi, K. Sato, H. Ohki, and T. Kaneko, "Optically Accessible Microchannels Formed in Single-Crystal Silicon Substrate for Studies of Blood Rheology," *Microvascular Research*, vol. 44, pp. 226–240, 1992.

(List continued on next page.)

*Primary Examiner*—Frank G. Font
*Assistant Examiner*—Reginald A. Ratliff
*Attorney, Agent, or Firm*—John P. Hohimer

[57] ABSTRACT

A resonant-cavity apparatus for cytometry or particle analysis. The apparatus comprises a resonant optical cavity having an analysis region within the cavity for containing one or more biological cells or dielectric particles to be analyzed. In the presence of a cell or particle, a light beam in the form of spontaneous emission or lasing is generated within the resonant optical cavity and is encoded with information about the cell or particle. An analysis means including a spectrometer and/or a pulse-height analyzer is provided within the apparatus for recovery of the information from the light beam to determine a size, shape, identification or other characteristics about the cells or particles being analyzed. The recovered information can be grouped in a multi-dimensional coordinate space for identification of particular types of cells or particles. In some embodiments of the apparatus, the resonant optical cavity can be formed, at least in part, from a vertical-cavity surface-emitting laser. The apparatus and method are particularly suited to the analysis of biological cells, including blood cells, and can further include processing means for manipulating, sorting, or eradicating cells after analysis thereof.

28 Claims, 19 Drawing Sheets

OTHER PUBLICATIONS

V. V. Tuchin, "Lasers and Fiber Optics in Medicine," *Proceedings of the Society of Photoinstrumentation Engineers*, vol. 1981, pp. 2–16, 1992.

P. L. Gourley, K. E. Meissner, T. M. Brennan, and B. E. Hammons, "Surface–Emitting Semiconductor Laser Spectroscopy for Characterizing Normal and Sickled Red Blood Cells," *Proceedings of the Society of Photoinstrumentation Engineers*, vol. 2387, pp. 148–160. Mar. 1995.

K. E. Meissner, P. L. Gourley, T. M. Brennan, B. E. Hammons, and A. E. McDonald, "Surface–Emitting Semiconductor Laser for Intracavity Spectroscopy and Microscopy," *Proceedings of the Society of Photoinstrumentation Engineers*, vol. 2399, pp. 561–570, Jul. 1995.

P. L. Gourley, K. E. Meissner, M. F. Gourley and J. Lyo, "A Radically New Approach to Cell–Structure Analysis," *Biophotonics International*, pp. 48–56, Jul./Aug. 1995.

P. L. Gourley, A. E. McDonald, and M. F. Gourley, "Vertical Cavity Surface–Emitting Laser Scanning Cytometer for High Speed Analysis of Cells," *Proceedings of the Society of Photoinstrumentation Engineers*, vol. 2679, pp. 131–141, Jan. 29–30, 1996.

P. L. Gourley, M. F. Gourley, T. Bloclage, and M. Luke, "Vertical Cavity Surface–Emitting Laser Cytometer for Analysis of Cells," Presented at the 1996 Conference on Lasers and Electro–Optics (CLEO), Anaheim, CA, May 22–27 1996.

P. L. Gourley and M. F. Gourley, "A Biological Microcavity Laser," Presented at the International Quantum Electronics Conference (IEEE), Sidney, Australia, Jul. 14–19, 1996.

P. L. Gourley, "Semiconductor Microlasers: A New Approach to Cell–Structure Analysis," *Nature Medicine*, vol. 2, pp. 942–944, Aug. 1996.

K. E. Meissner, P. L. Gourley, T. M. Brennan, B. E. Hammons, and A. E. McDonald, "Intracavity Spectroscopy in Vertical Cavity Surface–Emitting Lasers for Micro–Optical–Mechanical Systems," *Applied Physics Letters*, vol. 69, pp. 1517–1519, 9 Sep. 1996.

5 nm

Intensity

Emission Wavelength

RESONANT-CAVITY APPARATUS FOR CYTOMETRY OR PARTICLE ANALYSIS

CROSS REFERENCE TO RELATED APPLICATIONS

This application is a continuation-in-part application of U.S. patent application Ser. No. 08/407,345 now U.S. Pat. No. 5,608,519 entitled "Laser Apparatus and Method for Microscopic and Spectroscopic Analysis and Processing of Biological Cells", to Paul L. Gourley and Mark F. Gourley, filed on Mar. 20, 1995.

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates generally to cytometry and particle analysis, and more specifically to a resonant-cavity apparatus and method for optical microscopic and spectroscopic analysis of biological cells or dielectric particles. Analysis is performed using a spontaneous emission or lasing light beam that is generated within a resonant optical cavity of the apparatus, with the light beam being encoded with information about one or more cells or particles located therein. An analysis means is provided within the apparatus for recovery of the information from the light beam to determine a size, shape, identification or other characteristics about the cells or particles being analyzed.

BACKGROUND OF THE INVENTION

In recent years, the need for high-speed automated or semi-automated analysis and processing of biological cells and cell components has been recognized. Such analysis and processing can include determination of morphologic characteristics of cells or differences in physical properties of cells, and is of special importance in the fields of cytochemistry, immunology, oncology, genetics, molecular biology and the like.

One method for analyzing and processing biological cells at high speed is flow or scanning cytometry wherein prepared cells are suspended in a carrier fluid and then are enclosed within an envelope or sheath stream and are passed one at a time through a sensing zone by hydrodynamic focusing. In the sensing zone, the cells are irradiated by a focused laser beam (with the cells being located outside of any optical or laser cavity); and a light detector is used to measure scattered, absorbed, or re-emitted fluorescent light. The effect that a cell has on the focused laser beam that it intercepts can be detected in a number of ways. In general, the cell has a refractive index which is different from that of the medium in which it is suspended. The cell will therefore scatter a portion of the incident laser light through a range of angles, and with varying intensities, that depend upon the refractive index difference between the cell and the surrounding carrier fluid, the cell size and shape, and any internal variations in refractive index and structure in the cell, as well as the wavelength of the illuminating light. A cell can also absorb some of the incident light, with a portion of the absorbed light being re-emitted as fluorescence, typically at an emission wavelength that is longer than the wavelength of the absorbed light. Light detectors can be arranged to measure different angular intervals of the scattered or fluorescent light.

Due to a low scattering efficiency of small biological cells (typically less than 15 microns in diameter) and also due to a limited number of sites from which fluorescence can occur, the number of photons detected for each cell moving through the focused laser beam can be small, especially compared to the number of photons in the incident focused beam. Therefore, the limits of sensitivity of the prior art flow cytometry methods for cell analysis and processing depend critically on the photon flux (i.e. power) of the incident laser beam, and the magnitude of the perturbations in the scattered or fluorescent light produced by different variants of the biological cells to be analyzed (e.g. normal versus abnormal cells).

An advantage of the present invention is that biological cells or other similarly-sized dielectric particles can be analyzed by locating the cells or particles within an analysis region inside an optical or laser cavity, with the cells acting in combination with a gain medium within the cavity to generate a light beam (comprising spontaneous emission or lasing light) having information about the cells impressed (i.e. encoded) thereupon.

Another advantage of the present invention is that information related to a size, shape, and dielectric constant of biological cells or dielectric particles can be impressed upon a generated light beam in the form of an emission spectrum, a transverse mode profile, an optical intensity, a pulse-height distribution, a nonlinear optical signal, a lasing threshold characteristic, or a combination thereof and subsequently recovered for analysis of the biological cells or dielectric particles. In the case of biological cells, the recovered information can be used for studies of cell activation, cell proliferation, or cell life cycles. The recovered information can be used to analyze internal characteristics of cells such as DNA, RNA, nucleohistones, mitochondria, golgi bodies, endoplasmic reticulum, lysozomes, and phagosomes.

A further advantage of the present invention is that information selective to a portion of a cell or to a particular constituent of the cell can be impressed upon a light beam and recovered in an analysis means, for analyzing the cell or for subsequent processing thereof.

Still another advantage of the present invention is that a biological cell or a dielectric particle can be selectively tagged with a fluorescent stain or a non-fluorescent marker (e.g. in the case of a cell, a monoclinal antibody that can act to modify the cell structure and function), with the fluorescent stain forming at least a part of the gain medium within a resonant optical cavity containing the cell or particle; so that upon activation of the gain medium, light can be generated at predetermined locations wherein the florescent stain or marker is localized.

Yet another advantage of the present invention is that a compact cytometer or particle analyzer can be formed according to the present invention comprising on a substrate one or more analysis regions for containing cells or particles to be analyzed, with light emission (spontaneous or lasing) being generated by a gain medium acting in combination with the cells or particles to impress information about the cells or particles onto the emitted light.

Another advantage of the present invention is that a compact biological cell analyzer and processor can be formed on a substrate having at least one inlet channel for introducing the cells substantially one at a time into one or more analysis regions wherein a light beam is generated having information about the cells impressed thereupon, and a cell processing regions proximate to each analysis region wherein different variants of the cells can be separated after analysis into a plurality of reservoirs and/or outlet channels.

These and other advantages of the apparatus of the present invention will become evident to those skilled in the art.

SUMMARY OF THE INVENTION

The present invention relates to a resonant-cavity apparatus for analyzing cells or particles that comprises a resonant optical cavity formed by at least two reflecting mirrors and including a semiconductor gain medium and an analysis region for containing one or more cells or particles to be analyzed; and pump means for activating the gain medium to generate light (either spontaneous emission or lasing light), with the light having information about the cell or particle encoded thereupon.

The apparatus according to the present invention can further comprise analysis means for receiving or detecting the light beam and recovering the information about the cells or particles. The analysis means can include one or more elements selected from the group consisting of a spectrometer for analyzing a spectral distribution of the light beam, a camera for analyzing a spatial distribution of the light beam, a detector for analyzing an intensity of the light beam, and a pulse-height analyzer for analyzing a pulse-height distribution of the intensity of the light beam. The analysis means can further provide one or more outputs for display or for activating processing means for processing of the cells or particles in response to information derived therefrom. (Processing of cells or particles is defined herein to include sorting or manipulating according to size, shape, composition, or variants thereof; or removing abnormal cells by laser eradication.)

In some embodiments of the present invention, the apparatus can include a flow cell for transporting the biological cells or dielectric particles substantially one at a time through the analysis region within the resonant optical cavity, or a plurality of parallel or interconnected flow cells for simultaneously analyzing and processing many cells or particles. In other embodiments of the present invention, the resonant optical cavity can comprise a pair of optically-coupled sub-cavities, with one of the sub-cavities containing the semiconductor gain medium, and the other of the sub-cavities containing the analysis region.

Additional advantages and novel features of the invention will become apparent to those skilled in the art upon examination of the following description, or can be learned by practice of the invention. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
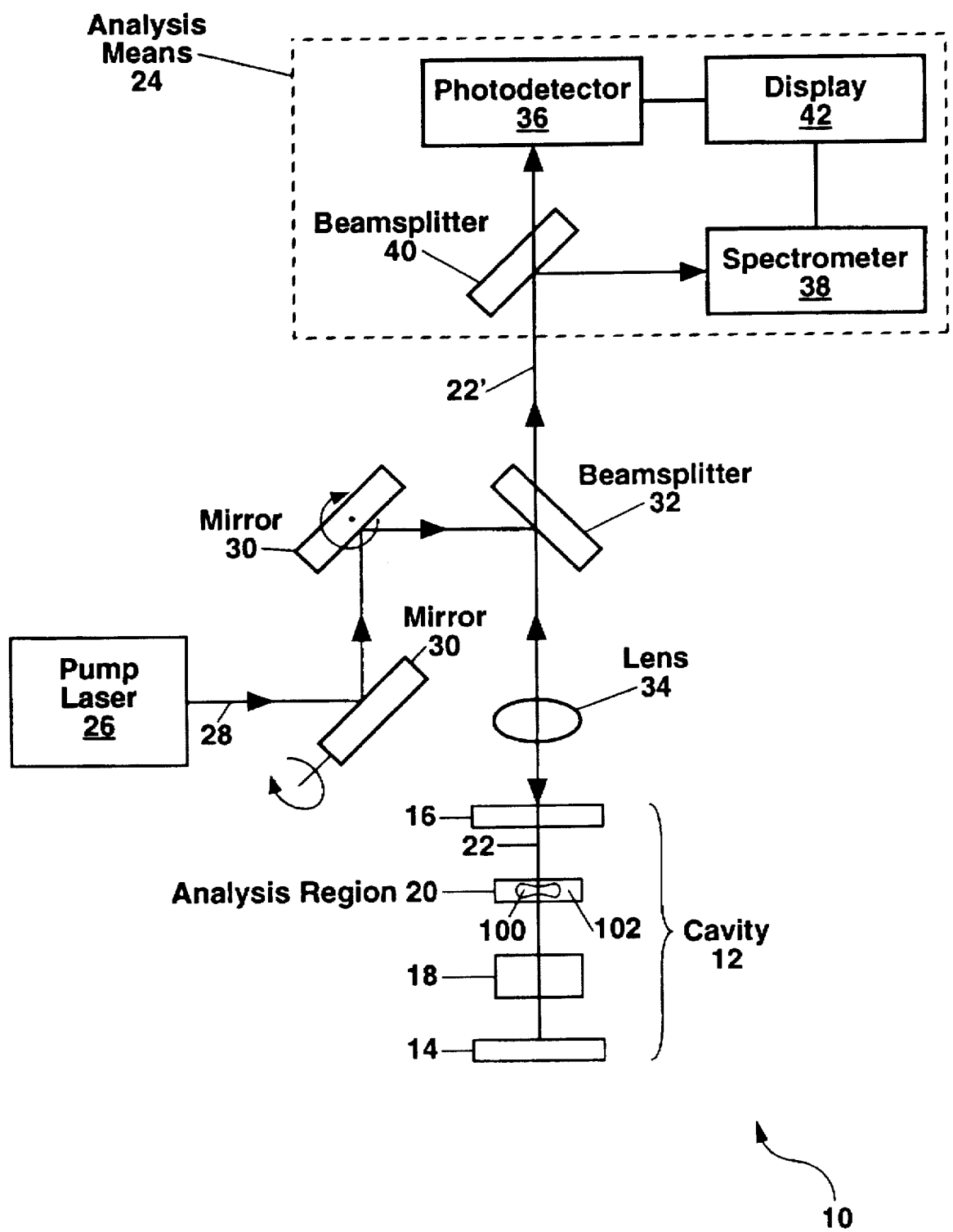
FIG. 1 shows a schematic diagram of a first embodiment of an apparatus for analyzing biological cells or dielectric particles according to the present invention.

Referring to FIG. 1, there is shown a schematic diagram of an apparatus for analyzing cells or particles according to the present invention. The apparatus 10 comprises a resonant optical cavity 12 formed by at least two reflecting mirrors (e.g. a lower mirror 14 and an upper mirror 16), a gain medium 18 within the cavity, and an analysis region 20 within the resonant optical cavity 12 for locating at least one biological cell or dielectric particle 100 to be analyzed. Pump means are provided for activating the gain medium 18 for generating optical gain within the cavity for emission of a light beam 22 (either a spontaneous emission beam or a laser beam), with the light beam 22 having impressed thereupon information about the cell or particle 100 being analyzed. The apparatus can further comprise analysis means 24 for receiving a portion 22' of the light beam 22 and recovering the information about each cell or particle 100 being analyzed.

Figure 3A:
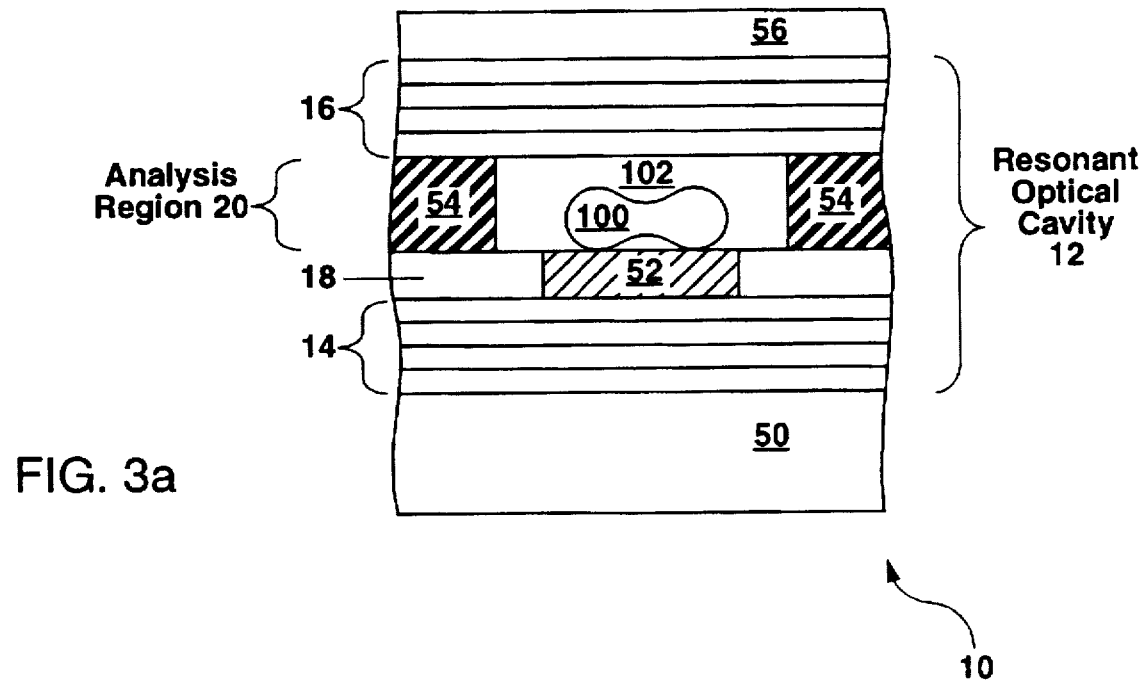
FIGS. 3a and 3b show first and second examples, respectively, of an apparatus for analyzing cells or particles according to the present invention.
Figure 3B:
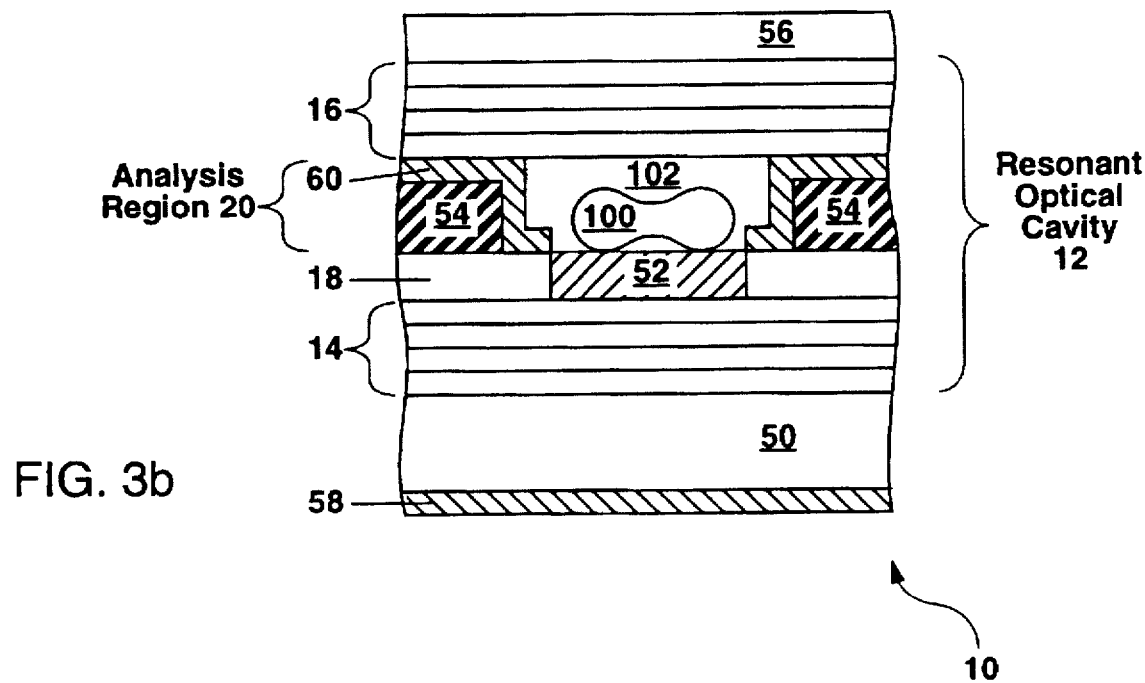
Figure 19:
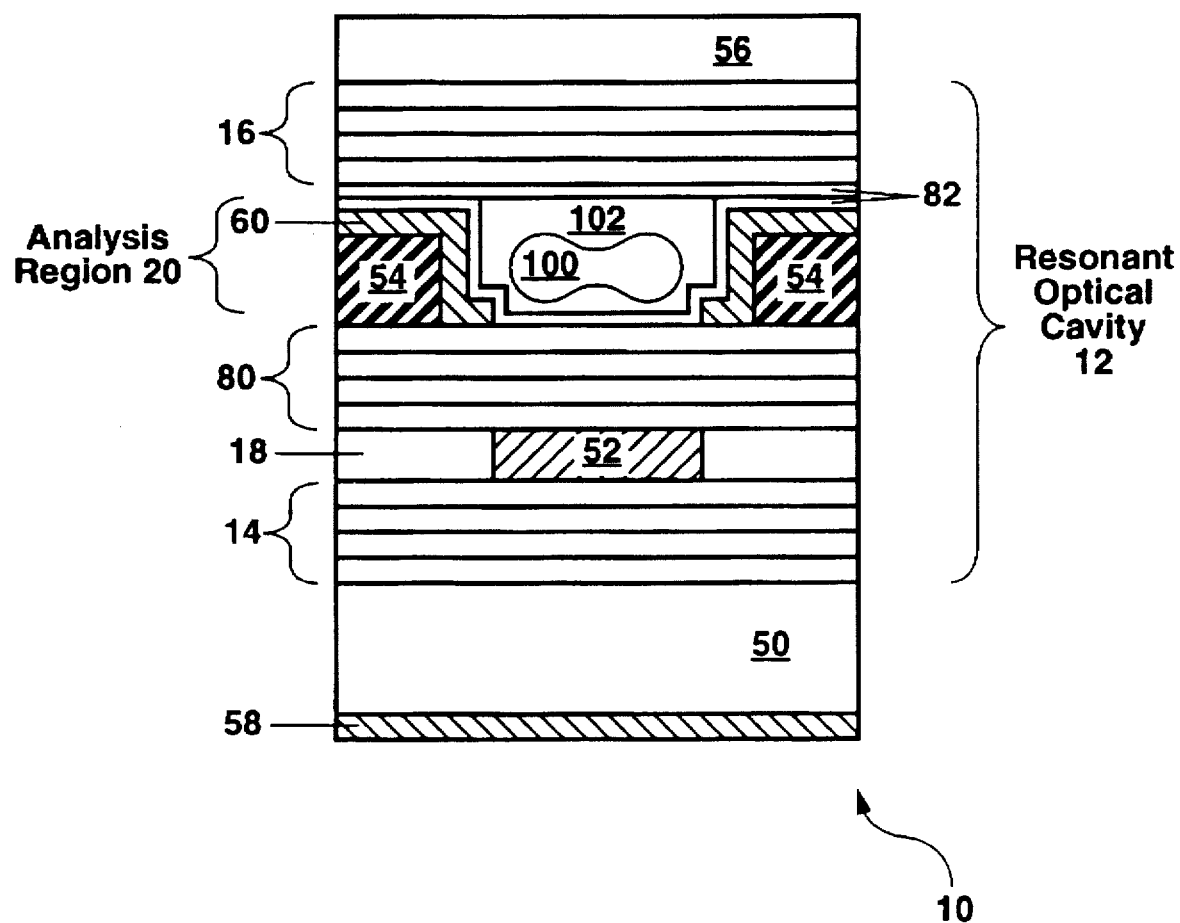
FIG. 19 shows a fourth example of an apparatus for analyzing cells or particles according to the present invention.

The gain medium 18 preferably generates light at a wavelength that is at least partially transmitted through each cell or particle 100 to be analyzed. In general, a gain medium 18 for generating light at a wavelength of about 600 to 1500 nanometers is to be preferred since many biological cells and carrier fluids 102 for transporting cells or particles 100 are at least partially transparent over this wavelength range. In other embodiments of the present invention, a wavelength range for operation of the apparatus 10 can be predetermined between about 0.2 and 10 microns depending upon the type, size and characteristics of the cells or particles 100 to be analyzed. The types of gain media 18 that can be used for practice of the present invention include gas, organic dye, solid state, and semiconductor gain media. Vertical-cavity surface-emitting semiconductor lasers as shown in FIGS. 3a and 3b and FIG. 19 are especially well-suited for forming, at least in part, the resonant optical cavity 12 of the present invention, and for providing optical gain for generating the spontaneous emission or lasing light beam 22. (The resonant optical cavity 12 generally forms a laser structure that can be operated below a threshold for lasing to generate a spontaneous emission light beam 22, or above the threshold for lasing to generate a lasing light beam 22.)

The resonant optical cavity 12 includes a pump means for activating the gain medium 18. The pump means can be an optical pump means comprising a pump laser 26 (as shown in FIG. 1) or a lamp for activating a gain medium 18 in an organic dye, solid state, or optically-pumped semiconductor cavity 12. Alternately, the pump means can be an electrical current flowing through a semiconductor p-n junction as in an electrically-injected semiconductor cavity 12 such as a vertical-cavity surface-emitting laser; or an electrical current flowing across a discharge as in a gas laser cavity 12. The pump means can be operated either continuously or in a pulsed mode to generate either a continuous-wave (cw) or pulsed light beam 22. A pulsed pump means including a nanosecond, picosecond, or femtosecond pump laser 26 can be used for excitation of an optically-pumped laser cavity 12.

In the case of an optical pump means for activating the gain medium 18 as shown in FIG. 1, a pump laser 26 provides a pump beam 28 that can be directed through a partially transmitting or dichroic upper mirror 16 into the gain medium 18, for example, by a pair of beam directing mirrors 30, a beamsplitter 32 (or otherwise a dichroic mirror that substantially reflects the pump beam 28 while substantially transmitting the portion 22' of the light beam 22 to the analysis means 24), and a lens 34. The pump beam 28 is preferably focused into a small spot of about 100 microns or less within the gain medium 18. Each beam directing mirror 30 preferably includes steering means such as a galvanometer, an acousto-optic beam deflector, an electro-optic beam deflector, or the like for steering the pump beam 28 to activate a particular portion of the gain medium 18. The optical pump means can be directed through a microscope, with the beamsplitter 32 and the lens 34 being part of an optical train within the microscope.

For practice of the present invention for analyzing cells or particles 100, the pump beam 28 is preferably directed into the gain medium 18 so that the activated portion of the gain medium lies along a central portion of the resonant optical cavity 12 in line with the analysis region 20 so that one or more cells or particles 100 can form a lens, optical waveguide, or dispersive optical element to redirect light rays within the cavity, thereby leading to the generation of the light beam 22 and encoding the beam with information about each cell or particle 100. It should be noted that under normal operation of the apparatus 10, the cells or particles 100 are instrumental in generating the light beam 22 and in no way acts to extinguish a pre-existing light beam. This differentiates the present invention from other types of laser particle analyzers in which the presence of a particle acts to interrupts or extinguishes a lasing beam.

The analysis region 20 is located within the resonant optical cavity 12 as shown in FIG. 1. The analysis region 20 can be in the form of a container for holding one or more cells or particles 100 in a fixed position; or the analysis region 20 can be a channel region of a flow cell for transporting cells at a high-speed through the apparatus 10. For an analysis region 20 in the form of a container, the lateral dimensions of the analysis region can be many times larger than the size of the cells or particles 100 to be analyzed so that a plurality of cells or particles 100 can be placed in the analysis region (with the cells preferably in a carrier fluid 102) and individually analyzed, for example, by steering the pump beam 28 to the location of a particular cell or particle 100 and thereby activating the portion of the gain medium 18 in superposition with the cell or particle. After the analysis of a particular cell or particle 100, the pump beam can be steered to different locations within the analysis region 20 for the analysis of other cells or particles 100.

The analysis region 20 can also be a channel region of a flow cell. In this case, the channel region can have transverse dimensions perpendicular to a flow direction that are constricted to dimensions down to about twice the size or less of the cells or particles to be analyzed so that the cells or particles 100 can be transported in a carrier fluid 102 substantially one at a time through the central portion of the resonant optical cavity 12 for analysis thereof. The channel region can be further constricted in one or more transverse dimensions for orienting the cells or particles 100 in a particular direction. For example, when processing red blood cells (i.e. erythrocytes) that have a biconcave shape, the channel height (i.e. the transverse dimension of the analysis region oriented parallel to the light beam 22 in FIG. 1) is preferably about 5 microns or less to orient the cell as shown in FIGS. 1–3. In general, the transverse dimensions of the channel region will be predetermined depending upon the types or variants of cells or particles to be analyzed and processed by the apparatus 10. In some embodiments of the present invention, the channel region can be widened so that a plurality of cells can be transported at the same time through the central portion of the resonant optical cavity 12, with a pump laser beam 28 being steered to the location of each cell for analysis thereof.

When the analysis region 20 is a channel region of a flow cell (e.g. for cytometry), means for supplying biological cells 100 to the analysis region can be connected to one side of the flow cell (i.e. to an inlet channel), and means for accumulating the cells can be connected to the other side of the flow cell (i.e. to an outlet channel). The means for supplying the biological cells 100 to the analysis region can be positive displacement pumps, or syringes, or the like; and such supply means can transport the cells 100 through the analysis region 20 at a variable rate, or at a controlled high speed. In some embodiments of the present invention, an electric field (e.g. directed along a transport or flow direction) or capillary action can be used to transport the cells or particles 100 to or through the analysis region 20. The means for accumulating the biological cells 100 can include one or more cell processing regions, or means for processing a plurality of cells wherein the cells 100 are selectively tagged or sorted in response to information gathered by the apparatus 10 (e.g. in response to signals received from the analysis means 24).

The cell processing means can provide for sorting of cells 100 according to variants thereof, or for removing abnormal cells 100 by laser eradication, or for other manipulations of cells according to identity, size, shape, variants, composition, or the like. The cell processing means can include, for example, a nozzle mounted upon a piezoelectric transducer for converting a flow stream in a flow cell of the apparatus 10 into a plurality of constant volume droplets, each droplet containing a cell 100 to be processed. The cell processing means can electrically charge the individual droplets in response to a signal received from the cell analysis means 24, with the cells 100 then being directed through a static electric field whereby droplets with different charges are deflected into different reservoirs or flow channels of the cell processing means. Such processing of cells by means of an electric field is commonly used in the art of flow cytometry (but with the cells being located outside of any laser cavity), and is disclosed, for example, in U.S. Pat. No. 4,765,737 to Harris et al.

The cell processing means can further include one or more manipulation lasers for manipulating, sorting, or eradicating the cells during processing thereof. The use of laser beams for the manipulation or sorting of cells (e.g. so called "optical tweezers") is disclosed in an article by A. Ashkin, J. M. Dziedzic, and T. Yamane entitled "*Optical Trapping and Manipulation of Single Cells Using Infrared Laser Beams*," published in Nature, volume 330, pages 769–771, December 1987; and in a book entitled "Noninvasive Techniques in Cell Biology," edited by J. K. Foskett and S. Grinstein, chapter 15, pages 375–402, published by John Wiley, 1990.

Cell or particle manipulation, sorting, or the like can be performed by the use of a focused laser beam (preferably at an infrared wavelength) that acts to trap or entrain a cell or particle within the focused laser beam and thereby allow the cell or particle to be moved by optical radiation pressure (i.e. photon momentum) at velocities of up to about 500 $\mu m\text{-}s^{-1}$ or more as the laser beam is steered. In this manner a plurality of cells or particles 100 in a carrier fluid 102 can be manipulated or sorted after analysis according to identity, size, shape, variants, composition, or the like, and transferred to different reservoirs or flow channels as shown in a third example of the present invention in FIG. 4.

Another form of cell processing that can be practiced according to the present invention is cell eradication in which a laser beam is used at a power level of about 50 to 100 milliWatts or more to destroy a biological cell 100 after analysis. For laser eradication of cells, it is generally preferable to use a laser operating at ultraviolet or visible wavelengths since cells have a higher absorption at these wavelengths as compared to infrared wavelengths. Furthermore, the laser manipulation of cells by optical trapping can be substantially modified or enhanced by the presence or absence of a multi-beam interference effect within the resonant optical cavity 12.

In FIG. 1, the portion 22' of the light beam 22 generated in the resonant optical cavity 12 (due to the presence of a cell or particle 100 within the central portion of the cavity) is directed into the analysis means 24 for microscopic and/or spectroscopic analysis of the cell. The analysis means 24 can be beam-coupled or fiber-coupled to the beam 22', and preferably includes a photodetector 36 and a spectrometer 38 for microscopic and spectroscopic analysis, respectively wherein the information about the cells or particles 100 is recovered. The analysis means 24 can further include a beamsplitter 40 or the like for dividing the beam 22' into two or more analysis beams. The analysis means 24 also preferably includes a display 42 which can include a computer or the like for receiving outputs from the photodetector and spectrometer and digitizing, recording, and displaying the information recovered from the cells; and/or comparing the recovered information with a look-up table for identifying identity, size, shape, variants, composition, or the like; and for providing one or more output signals to the cell processing means for subsequent processing of the cells.

In some embodiments of the present invention, the analysis means 24 can be part of an existing microscopic analysis system (e.g. a microscope), with the analysis means 24 being as simple as an imaging camera 36 and a television monitor 42. In this case, the apparatus 10 can be used, for example, for a manual microscopic analysis of cells or particles 100, with images of the cells or particles 100 viewed in real time at a video rate.

In other embodiments of the present invention, the analysis means 24 can be compactly formed (e.g. as an array photodetector 36 and/or a spectrometer 38 integrated on a semiconductor chip) so that the analysis means can be located near or incorporated with the resonant optical cavity 12 and the analysis region 20, thereby forming a compact or integrated apparatus 10 for cell or particle analysis or processing.

Microscopic analysis can be performed with the photodetector 36 which can be a single-element detector such as a photodiode or photomultiplier tube or the like for measuring an optical intensity of the portion 22' of the laser beam 22 incident upon the photodetector. Alternately, the photodetector can be a one- or two-dimensional detector array of photodiodes or a charge-coupled detector (CCD) forming an imaging camera for measuring a transverse mode profile of the incident portion of the light beam 22. Such an imaging camera can provide a video display for the operator, thereby allowing the operator to observe operations during the processing and analysis of a plurality of cells or particles 100. The video display can include white- or infrared-light reflectance or transmittance images of cells as well as images of the incident portion 22' of the light beam.

A spectroscopic analysis of the portion 22' of the light beam 22 can be performed with the spectrometer 38 which can include a diffraction grating, prism, or the like for dispersing the portion 22' into its component wavelengths, and a one-dimensional array photodetector for detecting those components to generate a spectrum thereof. The spectrometer 38 can be a stand-alone instrument used with the apparatus 10; or the spectrometer can be integrated into the apparatus in a hybrid or integrated fashion (e.g. as an optical integrated circuit). The spectrometer 38 can also operate in real time at a video rate for display and/or analysis of the spectrum.

Figure 2A:
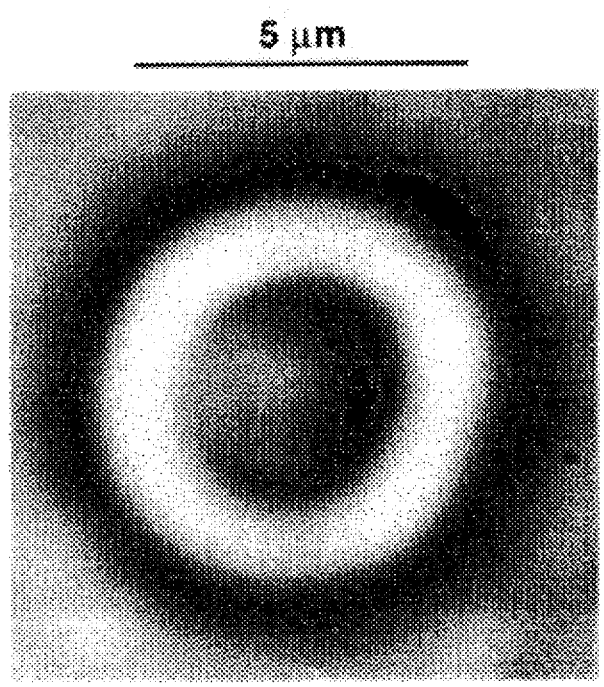
FIG. 2a shows a transmitted light image of a normal human red blood cell illustrating that different portions of a cell can redirect light differently.
Figure 2B:
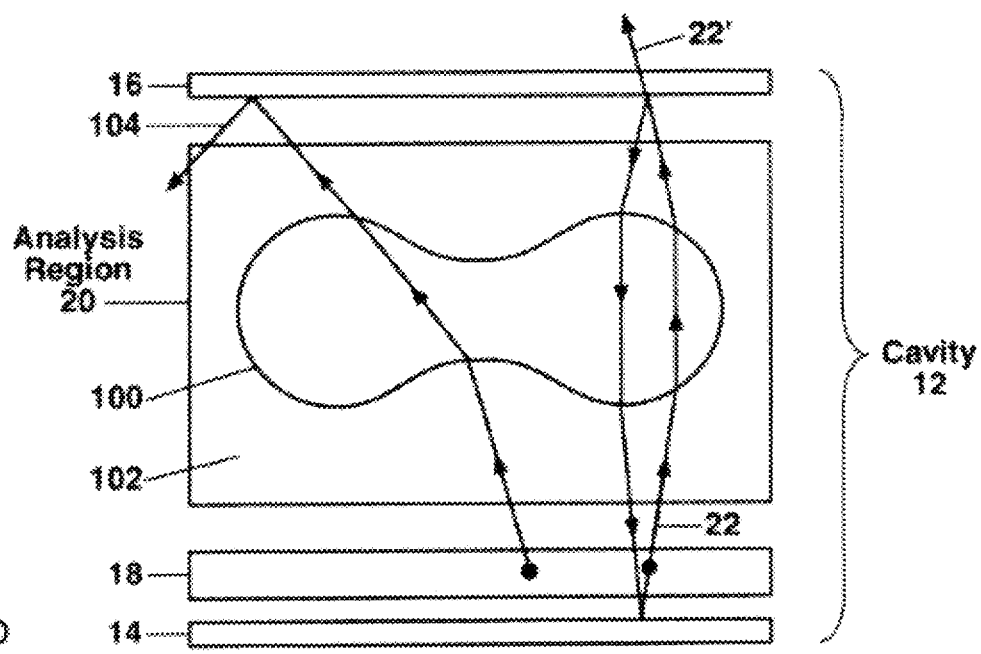
FIG. 2b shows a schematic illustration of a red blood cell within the analysis region of the apparatus of FIG. 1 to illustrate how the red blood cell redirects light rays within the apparatus and defines, at least in part, the location and shape of a light beam generated in the apparatus.

The present invention can be understood with reference to FIGS. 2a and 2b. FIG. 2a shows a photograph of a normal human red blood cell 100 recorded in transmission with an infrared light source. Normal red blood cells 100 have the shape of biconcave disks with a diameter of about 7 µm and a thickness of about 2 µm. The red blood cell in FIG. 2a has a relatively smooth outer surface defined by a cytoskeletal network of spectrin with a very small surface roughness (less than 50 nm) so that optical scattering is low. The surface includes a convex region near the cell circumference and a concave central region as shown in a side view of the cell in FIG. 2b. The interior of the red blood cell is relatively transparent at an infrared wavelength of, for example, about 850 nm so that the cell can be viewed as a lens with a focal length that varies across the cell diameter (or alternatively as an optical waveguide).

In FIG. 2a, the bright annulus in the transmitted light image corresponds to the convex region of the red blood cell (with a side view substantially as shown in FIG. 2b). In this region, the cell acts as a lens to redirect or focus the transmitted infrared light in a direction substantially normal to the top surface of the cell, allowing the light to be imaged in the photograph of FIG. 2a. However, in the concave central region of the cell in FIG. 2a, the transmitted infrared light is redirected off-axis so that this portion of the transmitted light image appears dark.

This lens-like nature is typical of many types of normal or abnormal cells including red and white blood cells, platelets, muscle cells, neural cells, sperm cells, and the like) with or without a nucleus; and it is also characteristic for many types of smooth-shaped dielectric particles (e.g. microspheres or microballoons). This lens-like nature is due to the relatively high optical transmission of cells or particles 100 and to the difference in the refractive index of the cells or particles 100 compared to a surrounding carrier fluid 102.

The refractive index of a red blood cell 100 is determined primarily by a complex formed by the internal hemoglobin and outer spectrin layer. The complex has a refractive index that is about 2% higher than a carrier fluid 102 such as a blood plasma that can surround the cell. The refractive indices of the internal hemoglobin and the outer spectrin are nearly identical. At an infrared wavelength of about 850 nm, the absorption coefficients of hemoglobin and water are both less than $10^{-2}$ cm$^{-1}$. Thus, red blood cells at infrared wavelengths can be considered to be nearly perfect optical elements (i.e. lenses) with little optical scatter or loss. Due to this high optical quality, the cells can be used as intracavity optical elements within the resonant optical cavity 12 to aid in generating a light beam 22.

Other types of biological cells 100 show similar infrared light transmission effects, although the contrast can be reduced compared to the red blood cell of FIG. 2a. For example, a white blood cell (i.e. a leukocyte) can comprise three bright inner regions corresponding to segments of the nucleus within the white blood cell. The same optical focusing effects, though at lower contrast, are present in cells in their hydrated physiologic state.

This is further illustrated in FIG. 2b which shows a schematic side view of the resonant optical cavity 12 with a red blood cell 100 surrounded by a carrier fluid 102 such as a blood plasma in the analysis region 20 within the cavity. For red blood cells, the refractive index of hemoglobin is about 1.40 compared to about 1.35 for blood plasma. Thus, the entire red blood cell can act as a lens inside the cavity 12. In the case of a white blood cell, a DNA/protein complex in the nucleus of the cell 100 has a higher refractive index than the surrounding cytoplasm, thereby acting as a lens. Furthermore, the white blood cell as a whole has a higher refractive index than the surrounding carrier fluid and can act as a lens also. Thus the white blood cell 100 can have two lens-like entities (i.e. the entire cell and the nucleus within the cell); with each lens-like entity acting in the apparatus 10 to produce a distinct set of transverse lasing modes (as shown in FIG. 10) which can be used to analyze and process a plurality of white blood cells. Other lens-like entities in a white blood cell can be formed by components of the cell including the nucleolus, golgi bodies, and endoplasmic reticulum.

The net result in FIG. 2b is that light passing through any biological cell 100 can be concentrated or channeled into the higher-refractive-index regions of the cell. This can be observed with only a single pass of infrared light through the cell as in the transmitted light image of FIG. 2a. Similar effects can be observed for dielectric particles (e.g. microspheres or microballoons) that are generally transparent and have a smooth surface curvature (i.e. a surface roughness smaller than a wavelength of the light generated by the apparatus 10).

In FIG. 2b, the gain medium 18 upon activation by the pump means generates a plurality of photons which are emitted out from the gain region. Some of these photons can be redirected through a portion of the cell 100 along a substantially closed path between the reflecting mirrors (14 and 16) to resonate within the cavity, stimulating the emission of additional photons and leading to amplified spontaneous emission or lasing action and the generation of a light beam 22. Other photons can be redirected through other portions of the cell 100 in an off-axis direction (e.g. along the path 104 in FIG. 2b) so that no closed path between the reflecting mirrors occurs, with the result that no enhancement in the light beam 22 is generated from these other portions of the cell 100.

Figure 5:
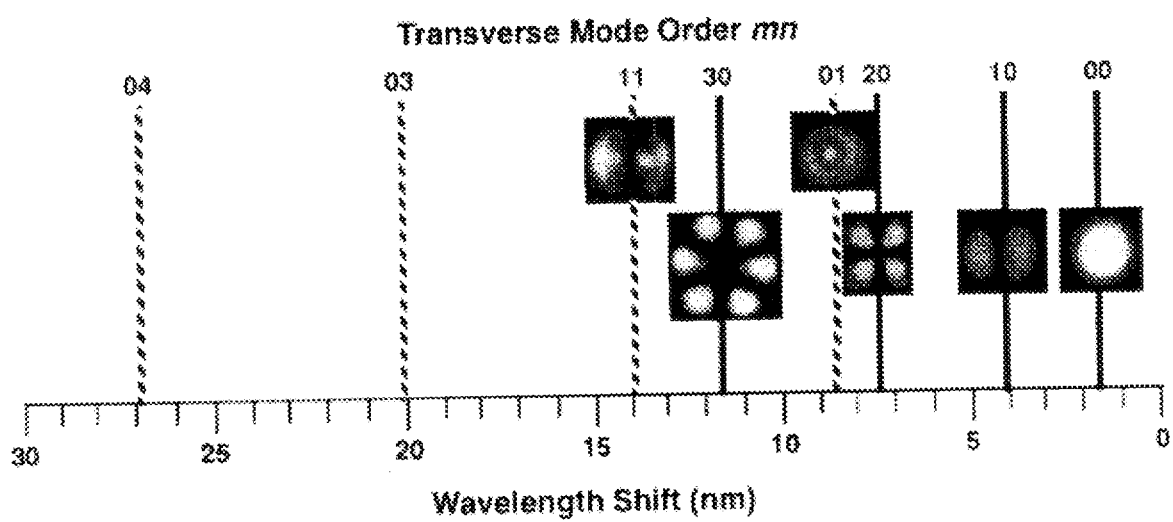
FIG. 5 shows calculated wavelength shifts due to a normal human red blood cell in the apparatus measured relative to the unperturbed laser cavity, with the inset photographs showing transverse mode profiles of lasing light generated by the apparatus and encoded with information about the red blood cell.

Thus, portions of cells and particles 100 can act as lenses or optical waveguides to increase an optical confinement of light generated within the gain medium 18 in a resonant optical cavity 12. By placing the cells or particles 100 inside the resonant optical cavity 12, the effect of even small differences in refractive index or shape can be amplified, resulting in the generation of a light beam 22 having emission characteristics defined, at least in part, by the cells or particles 100. In the case of transverse modes of a lasing light beam 22, those transverse modes that are stable can be theoretically calculated by a ray tracing analysis which allows a wavelength shift (relative to a fundamental lasing mode of the laser cavity in the absence of any cell or carrier fluid) for each stable mode to be determined and plotted as shown in FIG. 5. This transverse mode analysis is described in detail in a paper by P. L. Gourley, K. E. Meissner, T. M. Brennan, and B. E. Hammons entitled "Surface-Emitting Semiconductor Laser Spectroscopy for Characterizing Normal and Sickled Red Blood Cells," published in the Proceedings of the Photonics West '95 Conference, volume 2387, pages 148–161, by the Society for Photoinstrumentation Engineers.

From the illustration of FIG. 2b, it can be seen that the light beam 22 can have information impressed thereupon about a cell or particle 100 by placing the cell or particle 100 within an analysis region 20 inside the resonant optical cavity 12. This information can be recovered by measuring an emission spectrum, a transverse mode profile, an optical intensity, a pulse-height distribution or combinations thereof of a portion 22' of the light beam 22 with the analysis means 24 of FIG. 1. By generating an amplified spontaneous emission or lasing light beam 22 in the apparatus 10 of the present invention, a much larger analysis light signal (i.e. a larger photon flux) can be generated than can be possible for prior art analysis methods as described heretofore in which the cells are located outside any optical or laser cavity, with the analysis signal being in the form of scattered or re-emitted fluorescent light.

In the example of FIG. 2b, the cell or particle 100 (or components thereof) can also be tagged prior to being placed into the analysis region 20 or transported thereto. By preselecting a fluorescence stain that can be excited by a pump laser 26 to emit at a wavelength matched to the gain medium 18, the fluorescence emission generated within the cell can be additive to the gain produced within the gain medium 18, thereby increasing the amount of amplified spontaneous emission generated within the resonant optical cavity 12 and lowering a threshold for lasing. The fluorescence stain can thereby aid in impressing (i.e. encoding) information about the cells or particles 100 upon the light beam 22. For example, a selective staining of a biological cell 100 (including cell components) can be used to generate a lasing light beam 22 passing through the stained portions of the cell, thereby allowing the analysis of constituent matter within the cell, or aiding in the identification of cell variants. In some embodiments of the present invention, it can be possible to locate the gain medium as a fluorescent marker entirely within cells or particles 100 to be analyzed, thereby simplifying the construction of the resonant optical cavity 12 (for example, to simply a pair of reflecting mirrors surrounding an analysis region) and eliminating the need for a gain medium 18 separate from the cells or particles 100 to be analyzed.

FIG. 3a shows a first example of an apparatus 10 for analyzing cells or particles according to the present invention. In FIG. 3a, the resonant optical cavity 12 is in the form of an optically-pumped vertical-cavity surface-emitting semiconductor laser. The laser comprises a semiconductor substrate 50 upon which the resonant optical cavity 12 is formed. The resonant optical cavity 12 comprises a lower reflecting mirror 14, a semiconductor gain medium 18, a patterned analysis region 20, and an upper reflecting mirror 16.

The use of a semiconductor laser such as a vertical-cavity surface-emitting laser in FIG. 3 can be preferred for practice of the present invention due to the high gain available in a semiconductor gain medium 18 which can provide compensation for any absorption or scattering loss in the cells or particles 100 to be analyzed.

The semiconductor substrate 50 can be, for example, a III–V compound semiconductor such as gallium arsenide (GaAs), indium phosphide (InP), or the like as disclosed in U.S. Pat. No. 4,947,223 and references therein which are incorporated herein by reference; or the substrate 50 can be a micromachineable material such as silicon with a lower reflecting mirror 14 and a gain medium 18 formed thereupon or attached thereto. The lower reflecting mirror 14 preferably comprises a distributed Bragg reflector mirror formed from a plurality of alternating one-quarter-wavelength thick layers of high- and low-refractive-index semiconductor materials such as GaAs and aluminum-gallium-arsenide (AlGaAs), respectively. The lower reflecting mirror 14 can be formed on the semiconductor substrate or wafer by epitaxial growth methods such as molecular beam epitaxy (MBE), metal-organic chemical vapor deposition (MOCVD), or the like. The lower reflecting mirror 14 can have a reflectivity at a lasing wavelength of about 95 to 99% or more. As an example, a lower reflecting mirror 14 can be formed from 28.5 periods of alternating layers of low-index AlAs (about 620 nm thick) and high-index $Al_{0.2}Ga_{0.8}As$ (about 715 nm thick) for use at a lasing wavelength near 850 nm.

The semiconductor gain medium 18 can be grown above the lower reflecting mirror 14 by the same epitaxial growth method used for forming the lower mirror. The semiconductor gain medium 18 can comprise a bulk semiconductor such as GaAs or indium-gallium-arsenide (InGaAs) with a thickness of about 50 to 150 nanometers; or the gain medium 18 can include one or more quantum-well layers separated by barrier layers having an energy bandgap higher than the energy bandgap of the quantum-well layers to form a single- or multiple-quantum-well gain medium. In the latter case, the quantum-well layers can have thicknesses of about 5 to 30 nanometers; and the barrier layers can have a thickness up to about 250 nm. Unstrained or strained quantum-well layers and barrier layers can be used for forming the vertical-cavity surface-emitting semiconductor laser in FIGS. 3a and 3b. Furthermore, one or more quantum-well layers can be located at predetermined positions within the gain medium 18 to provide a periodic gain therein, or to position an electric field node or antinode within a particular part of the cavity (e.g. at the location of a particular component within one or more cells to be analyzed).

In FIG. 3a, an activated portion 52 of the gain medium 18 can be generated in response to a laser pump beam 28 propagating downwards through the upper reflecting mirror 16 into the gain medium 18. (The upper reflecting mirror 16 is preferably a dichroic mirror with a high transmission at a pump wavelength of the laser pump beam 28 and a high reflectivity at a resonant wavelength of the cavity 12.) The activated portion 52 can be circular or otherwise shaped (when viewed from above) with a size of about 20 to 100 microns or less, with the activated portion preferably being located in superposition with (e.g. below) a cell or particle 100 to be analyzed. The location of the activated portion 52 can be moved (e.g. within a large-area gain medium 18 having lateral dimensions of about 0.1 to 10 cm) by steering the pump laser beam 28 to a different location within the gain medium 18 for analyzing a plurality of cells or particles 100 in an analysis region 20 superposed with the gain medium.

The cells or particles 100 are preferably surrounded by a carrier fluid 102 (e.g. a buffered saline solution in the case of biological cells) within the analysis region 20 as shown in FIGS. 3a and 3b. The analysis region 20 in FIG. 3a is preferably formed above the gain medium 18 by etching down through semiconductor layers forming the resonant optical cavity 12, or by a deposition and patterning process, thereby forming a container or flow channel for one or more cells or particles 100. (Alternately, the analysis region 20 can be formed on the mirror side of the transparent substrate 56, for example, prior to depositing the upper reflecting mirror 16.) The process for forming the analysis region 20 can also form additional elements of the apparatus 10, including one or more flow channels, reservoirs, and processing regions.

The analysis region 20 can comprise, for example, a patterned insulating layer 54 formed by depositing or spinning on an insulating material (preferably including a biocompatible capping layer therein when biological cells are to be analyzed) such as silicon nitride, or silicon dioxide, or a photoresist, polyimide, glass, epoxy resin, or the like above the gain medium 18, and patterning the insulating layer to form one or more containers or flow channels therein. (The patterning of the insulating layer can be performed by an etching or lift-off process as known to the semiconductor processing art.)

In FIG. 3a, the upper reflecting mirror 16 is located above the analysis region 20, preferably forming a liquid-tight seal therewith. The upper reflecting mirror 16 can be a dielectric mirror formed, for example, from a plurality of alternating one-quarter wavelength layers of high- and low-refractive index dielectric materials deposited on a transparent substrate 56 such as glass, fused silica, sapphire, or the like. (Alternately, the upper reflecting mirror 16 can be formed on a semiconductor substrate 56 transparent to infrared light in a manner similar to the formation of the lower reflecting mirror 14.) The upper reflecting mirror 16 can be permanently attached to the analysis region 20 by means of an adhesive or the like to form, for example, a flow cell for transporting cells or particles 100 substantially one at a time through the analysis region; or the upper mirror can be detachable from the analysis region 20 for forming, for example, a static cell or container wherein one or more cells or particles 100 can be manually placed for analysis. In the case of a detachable upper mirror 16, the upper mirror can be held in place by gravity or by a clamp or the like, with or without forming a liquid-tight seal between the upper mirror 16 and the analysis region 20.

In some embodiments of the present invention, the lower reflecting mirror 14 and the gain medium 18 can be formed on a semiconductor growth substrate and subsequently removed therefrom (e.g. by polishing and/or etching away the growth substrate, or by selectively etching under the lower mirror and lifting off the lower mirror and gain medium) for attachment to a micromachined substrate 50 (e.g. a silicon substrate) for formation of the resonant optical cavity 12. This method is particularly applicable for the formation of an optically pumped cavity 12, and can be preferred for some embodiments of the present invention such as the compact biological cell analyzer and processor in the example of FIG. 4.

FIG. 3b shows a second example of an apparatus 10 for analyzing cells or particles according to the present invention. In FIG. 3b, the resonant optical cavity 12 is formed above a semiconductor substrate 50 to provide an electrically-injected vertical-cavity surface-emitting semiconductor laser. Such a laser can be formed, at least in part, in a manner similar to that described with reference to FIG. 3a. For an electrical excitation of the gain medium 18 in FIG. 3b (i.e. an electrical pump means), a p-n or p-i-n junction is formed within or surrounding the semiconductor gain medium; and the lower reflecting mirror 14 and the substrate 50 are both doped either n-type or p-type (to about $10^{18}$ cm$^{-3}$) with an impurity dopant. A lower electrode 58 can then be deposited below the substrate 50 (or below the gain medium 18), and an upper electrode 60 can be deposited above the gain medium. The upper electrode 60 can be a planar transparent electrode (e.g. indium tin oxide) overlying the gain region 18; or the upper electrode can overlie the patterned insulating layer 54 in the analysis region 20 as shown in FIG. 3b. (The upper electrode can be considered to be within the analysis region 20, and to form a part of the analysis region in the example of FIG. 3b). The upper electrode 60 preferably extends downward through the container or flow channel to contact an upper surface of the gain medium 18 (i.e. one side of the p-n or p-i-n junction) or a semiconductor layer provided thereabove. An electrical current can then be provided to flow between the lower and upper electrodes (58 and 60, respectively) to the p-n junction in the gain medium to generate optical gain in an activated portion 52 of the gain medium to promote lasing action in the laser cavity. Ion implantation or selective etching can be used to remove a portion of the gain layer beyond the activated portion for further defining the activated portion of the gain medium 18.

In the examples of FIGS. 3a and 3b, the light beam 22 (either in the form of a spontaneous emission light beam or a lasing light beam) is generated within the cavity 12 by the gain medium 18 acting in combination with one or more cells or particles 100 present within the analysis region 20. In the absence of any cells or particles 100, the light beam is less intense.

Figure 18A:
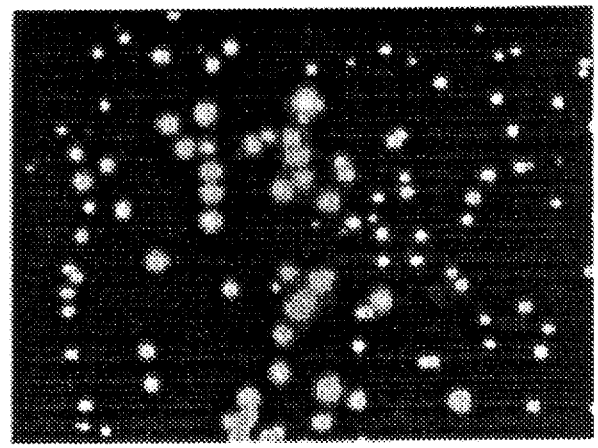
FIG. 18a shows an image of the sample of spherical particles of FIG. 16b generated with the apparatus of the present invention.
Figure 18B:
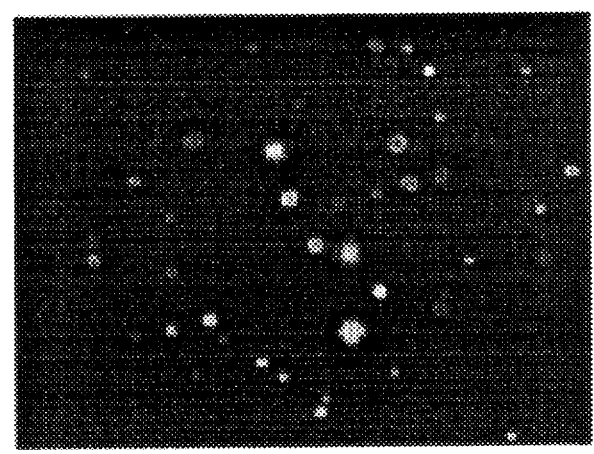
FIG. 18b shows an image of the sample of normal human red blood cells of FIG. 17b generated with the apparatus of the present invention.

The gain medium 18 can be activated by the pump means to provide a low gain for the cavity so that in the absence of any cell within the analysis region, the laser 12 is below a threshold for lasing so that a spontaneous emission beam 22 can be generated by the activated portion 52 of the cavity 12 for measurement with the analysis means 24. In this case, the spontaneous emission beam 22 can be amplified at the location of each cell or particle 100 due to the redirection of photons and improved waveguiding due to the lens-like nature of the cells or particles 100. In this way, the spontaneous emission beam 22 is encoded with information about the cells or particles 100 that are contained within the analysis region 20. Furthermore, the presence of a plurality of cells or particles 100 can be readily imaged with a camera since the cells or particles 100 generally appear as bright spots against a dim or dark background as shown in FIGS. 18a and 18b.

As an example, the cavity 12 can be operated below threshold with or without a cell present in the analysis region; and the introduction of a cell to the analysis region can act to locally alter a phase of the amplified spontaneous emission from the laser, thereby providing an analysis image of the cell or its components. Alternately, the gain medium 18 can be activated to provide a high gain for the cavity 12 so that a laser beam 22 is generated with or without a cell or particle 100 present in the cavity. In this case, the cell or particle 100 can encode information onto the generated laser beam 22 by altering or modifying an optical characteristic of the beam 22 such as an emission spectrum, a transverse mode profile, an optical intensity, a nonlinear optical signal (e.g. generated by polar molecules within the cell), a lasing threshold characteristic (e.g. the introduction of a cell into the analysis region can alter a threshold for lasing of the cavity 12, producing lasing within a below-threshold cavity), or a combination thereof. In any case, one or more optical characteristics of the laser beam 22 can be determined, at least in part, by portions of each cell or particle 100, thereby impressing or encoding information about the cell onto the laser beam 22.

Figure 4A:
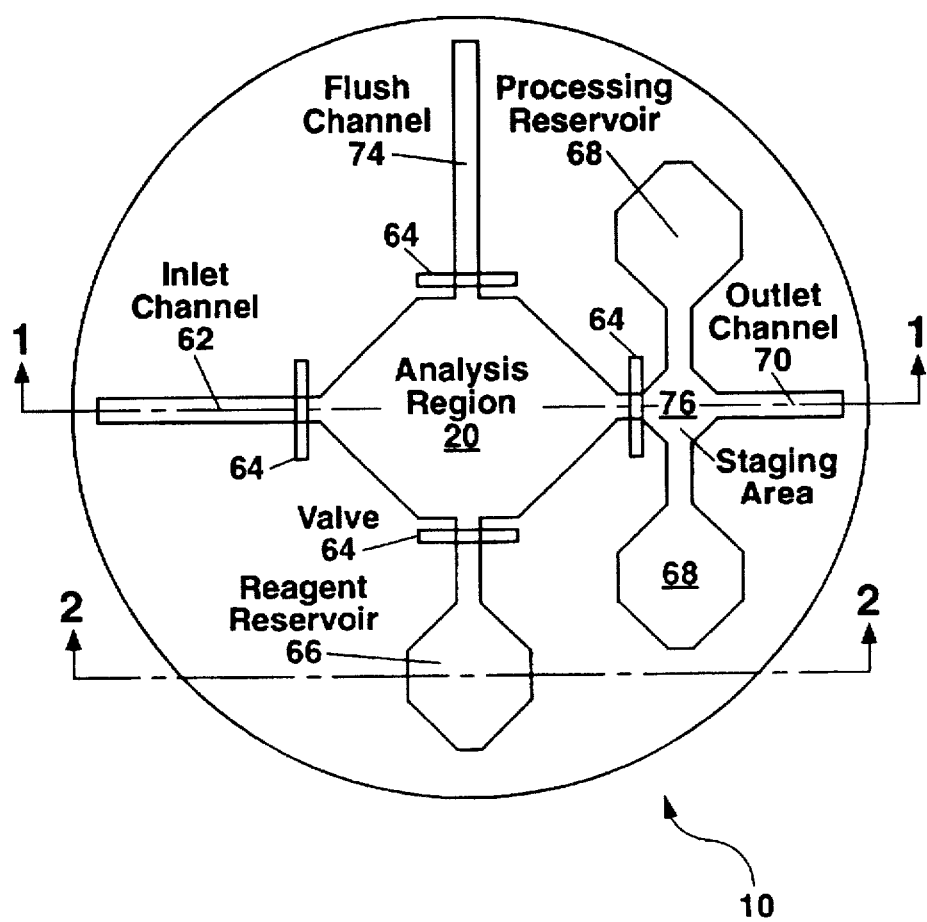
FIG. 4a shows a third example of an apparatus for analyzing cells or particles according to the present invention, including means for processing the cells or particles after analysis thereof.

FIG. 4 shows a third example of an apparatus 10 according to the present invention that is especially well suited for microscopic and spectroscopic analysis and processing of biological cells. In FIG. 4a, the apparatus 10 is formed as a compact device, preferably having an inlet channel 62 for admitting one or more biological cells 100 suspended in a carrier fluid 102 into the device. The inlet channel 62 can be connected to means for supplying the biological cells as described heretofore. The cells 100 upon entering the apparatus 10 can be transported through the inlet channel 62 to an analysis region 20 as shown in FIG. 4a. The analysis region can be capable of being isolated from the inlet channel 62 by a valve 64. The valve 64 can be, for example, a gate valve operated electrically (e.g. by an electrostatic motion of a hinged valve, or by a micromotor that is connected by a micromechanical gear train to move a valve gate between an open and a closed position), hydraulically (e.g. by a piston or gate moveable within the channel between an open and a closed position), or pneumatically (in a manner similar to a hydraulically operated valve 64), or optically (e.g. by the use of "photon tweezers" to move a particle or block of material between an open and a closed position in the channel) for opening and closing the valve 64 to allow the passage of one or more cells 100 therethrough. The valve 64 can be formed as a micromechanical device in a micromachineable substrate 50 (e.g. a silicon substrate) as known to the art of micromechanics.

The cells 100 to be analyzed can be transported into the analysis region 20 by the use of a flow stream in the inlet channel 62 for analysis thereof. The analysis region 20 can be connected by additional flow channels (with additional valves 64 which can be opened and closed for transport of the cells into and out from the analysis region 20) to additional regions of the apparatus including one or more reagent reservoirs 66, and one or more processing reservoirs 68 as shown in FIG. 4a. The reagent reservoirs 66 can be provided with agents such as cell stimulants, drugs, or reagents (e.g. monoclonal antibodies, or nucleic acids) that can modify cell properties; and these agents can be introduced into and/or flushed from the analysis region 20 by flow channels for analyzing a response of the cell 100 to these agents. A flush channel 74 can be provided for introducing fluids into and/or out from the analysis region 20 for cleansing thereof.

Figure 4B:
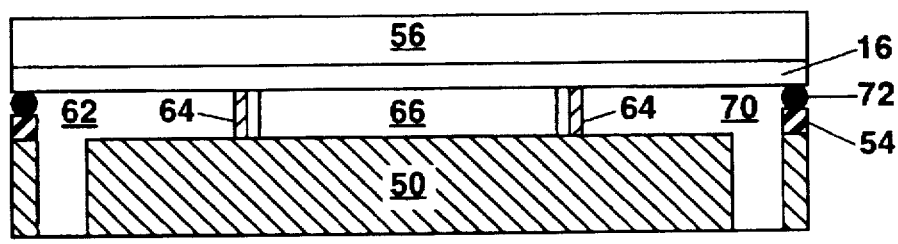
FIG. 4b shows a schematic cross-section view of the apparatus of FIG. 4a along the line 1—1.
Figure 4C:
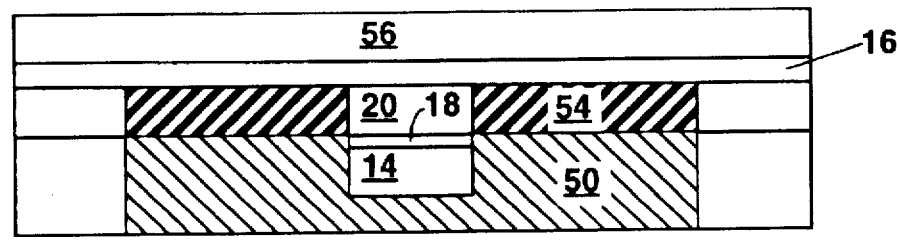
FIG. 4c shows a schematic cross-section view of the apparatus of FIG. 4a along the line 2—2.

In this example of the present invention, it can be preferable to fabricate the apparatus 10 on a micromachineable substrate 50 such as silicon or the like that allows the formation of the flow channels and valves by micromechanical processing as known to the art. In this case, the resonant optical cavity 12 can comprise a lower mirror 14 and a gain medium 18 that can be attached to the substrate 50 in an etched well thereof as shown in view 2 in FIG. 4c. The upper mirror 16 of the resonant optical cavity 12 can be formed on a transparent substrate 56 as described heretofore, with the transparent substrate being in contact with a patterned insulating layer 54 formed above the silicon substrate 50 as shown in FIGS. 4b and 4c. A liquid-tight seal 72 such as an o-ring or the like; or an adhesive can be provided between the patterned insulating layer 54 and the upper mirror 16 as shown in view 1 in FIG. 4b; or alternately, the surfaces of the layer 54 and the mirror 16 can be flat enough so that a liquid-tight seal can be formed when the insulating layer and upper mirror are brought into contact and held together by a clamp. One or more passivation layers (not shown) can be provided to line the analysis region 20 and surfaces contacted by the carrier fluid 102 for biocompatibility.

After analysis of the biological cells 100, the cells can be transported to a processing region comprising, for example, a pair of processing reservoirs 68 with a staging area 76 therebetween. The cells can be selectively manipulated, sorted, or eradicated in the staging area 76 of the processing region according to the information recovered from the cells by the analysis means 24. The apparatus 10 can further comprise one or more outlet channels 70 for clearing cells from the apparatus of for aiding in transporting the cells to and from the analysis and processing regions.

The compactness of the apparatus of FIG.4 (which can have lateral dimensions of a few inches or less) is advantageous in allowing the apparatus 10 to be positioned under a microscope for visual observation and/or for optically pumping the apparatus with a pump laser 26. The third example of the invention in FIG. 4 can have applications as a microlaboratory for conducting experiments in real time on biological cells. In addition, a plurality of parallel or interconnected laser biological cell analyzers 10 can be formed according to the present invention on a single substrate 50.

FIGS. 5–13 and 16–17 show calculations and measurements made according to the present invention, including measurements of normal and abnormal human red blood cells, normal human white blood cells, and dielectric particles. These calculations and measurements demonstrate the ability of the apparatus 10 to distinguish different sizes, types, and variants of cells and particles, and to selectively analyze constituents thereof.

FIG. 5 shows calculated wavelengths of transverse modes (i.e. eigenmodes) of the resonant optical cavity 12 under lasing conditions and including within the analysis region 20 a cell 100 having cylindrical symmetry (viewed along the direction of the laser beam 22) with a diameter of 7.5 μm and a refractive index of 1.4. (The wavelength shift in FIG. 5 is measured as a deviation from an unperturbed cavity wavelength of about 850 nm in the absence of any cell in the cavity 12.) In FIG. 5, the absolute wavelengths of the eigenmodes are given by:

$$\lambda_{lmn} = \frac{2\pi n_1}{\sqrt{\left(\frac{2\pi l - \phi}{2L}\right)^2 + \left(\frac{2 x_{mn}}{d}\right)^2}}$$

where $n_1$ is the refractive index of the cell (in a carrier fluid of refractive index $n_2$), $l$ is an integer corresponding to a longitudinal eigenmode, $\phi$ is a sum of the phases of the cavity mirrors located at positions $-L/2$ and $L/2$ along the cavity axis (denoted herein as the z axis), $x_{mn}$ is an nth zero of the mth Bessel function, and d is the cell diameter. Under normal conditions, the longitudinal modes in a vertical-cavity surface-emitting semiconductor laser cavity 12 can be spaced more widely than the gain spectrum so that only a single longitudinal mode lases in the unperturbed laser cavity. The transverse modes in the cavity 12, however, have a smaller wavelength separation so that a large number of transverse modes can support lasing. Furthermore, two polarizations corresponding to a transverse electric (TE) state and a transverse magnetic (TM) state can be associated with each transverse lasing mode.

The emission spectrum of the transverse lasing modes can be strongly influenced by the optical and structural properties of a cell or particle 100 placed within the cavity 12. A wavelength separation of the transverse modes from a given longitudinal wavelength (taken as zero wavelength shift in FIG. 5) is given by:

$$\Delta\lambda_{mn} = \frac{-\lambda^3 x_{mn}^2}{2\pi^2 n_1^2 d^2}$$

In the above equation, the wavelength separation, $\Delta\lambda$, of the transverse modes is dependent on the cell diameter, d, and also on the cell shape due to the $x_{mn}$ parameter (as shown in FIG. 5). The above equation for $\Delta\lambda$ is expected to be accurate for low-index transverse lasing modes (i.e. low values of m and n) for which the electric field of the beam 22 can be localized within the cell. For higher-index transverse lasing modes (i.e. high values of m and n), the electric field can extend beyond the cell boundaries; and the above model can be less accurate, with the wavelength separation, $\Delta\lambda$, being smaller than would be calculated from the above equation. Thus, the above equation for $\Delta\lambda$ shows that the emission spectrum of the light beam 22 can be used to recover information about the size and shape of the cell or particle 100, or components therein.

In FIG. 5, the inset photographs show experimentally measured profiles for the six lowest-order transverse lasing modes in the apparatus 10 with normal human red blood cells (of different sizes to stimulate lasing in the different transverse modes) in the laser cavity. Each image in FIG. 5 corresponds to a single transverse eigenmode of the cavity 12 as recorded with either a cw or nanosecond pulsed pump laser 26. With these pump lasers, the gain bandwidth of the gain medium 18 is small, and generally only one transverse mode is observed when the cavity 12 is lasing.

In FIG. 5, the transverse mode profile images show that the number of nodes and the lateral dimensions or spatial extent of a mode increases as the mode indices (m and n) increase. In FIG. 5, the mode indices, m and n, denote the number of angular and radial nodes (dark areas), respectively. In the samples of normal human red blood cells studied to date, the frequency of occurrence of a given mode depends on the distribution of cell sizes and shapes in a blood sample. The most frequently occurring transverse mode is the $TEM_{10}$ mode. This double-lobed mode is characteristic of about 50% of normal human red blood cells in a plasma carrier fluid in the physiologic state. Another common transverse lasing mode (not shown in FIG. 5) occurring in about 10% of normal human red blood cells is observed as a ring-shaped mode profile, and is designated $TEM_{10}*$ (where the star superscript denotes a linear combination of horizontal and vertical versions of the $TEM_{10}$ mode). Both the $TEM_{10}$ and $TEM_{10}*$ modes are consistent with the toroidal or biconcave shape of normal human red blood cells as shown in FIG. 2.

The fundamental $TEM_{00}$ mode in FIG. 5 occurs in only about 15% of normal human red blood cells, and is associated with cells that have lost some of their biconcavity; or with smaller blood cells. The higher-order transverse lasing modes $TEM_{20}$ (with a cloverleaf shape), $TEM_{30}$ (with a hexagonal shape), $TEM_{01}$ (with a dot and surrounding ring shape), and $TEM_{02}$ (with a split dot and ring shape) are observed much less frequently, each accounting for only a few percent of the total distribution of normal human red blood cells studied to date. These higher-order transverse lasing modes occur in the largest red blood cells for which the higher-order modes are stable.

Figure 7:
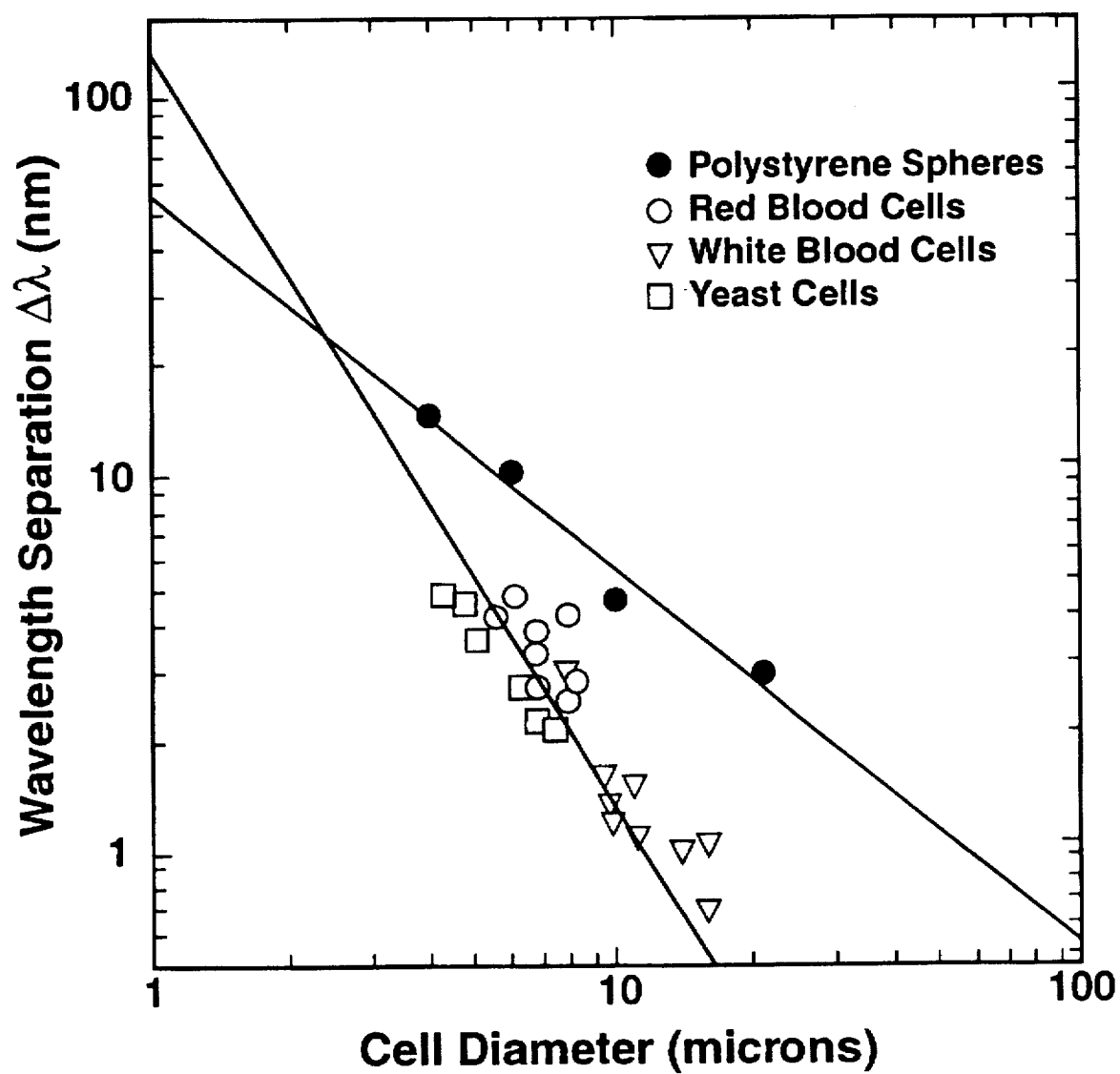
FIG. 7 shows a correlation of the diameter of different types of cells and particles and the wavelength separation, $\Delta\lambda$, between the $TEM_{00}$ and $TEM_{10}$ modes of a lasing light beam generated by the apparatus of the present invention.

A femtosecond pump laser 26 can also be used according to the present invention. In this case, the gain in the cavity 12 can be much larger and the gain bandwidth wider so that a plurality of transverse lasing modes can lase simultaneously in the lasing light beam 22. The observed distribution of intensities of each of the lasing modes will depend on the relative gain and loss for each mode, and can be measured with the spectrometer 38 in the analysis means 24. The relative optical loss in the cavity 12 of a particular transverse lasing mode will depend on the size, shape, and structure of the cell or particle 100, the ability of the cell or particle to redirect light rays, and any localized absorption or scattering losses therein. In general, the wavelength separation of the transverse modes will decrease with increasing cell or particle diameter, d, according to the above equation for $\Delta\lambda$, as shown in FIG. 7.

Figure 6A:
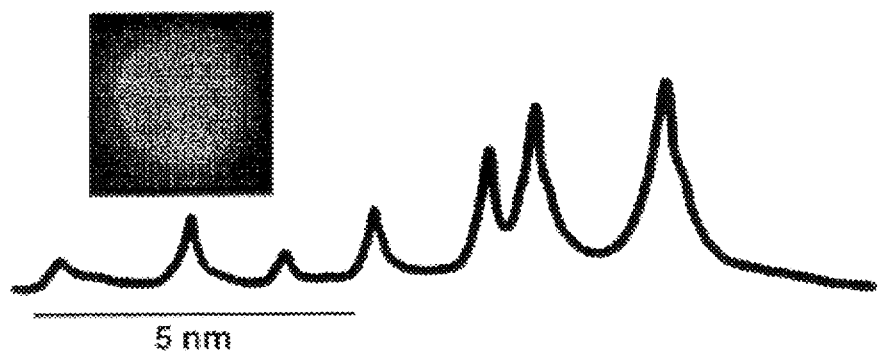
FIGS. 6a, 6b, and 6c show multimode emission spectra and transverse mode profiles generated by the apparatus of the present invention for different sizes of normal human red blood cells with the apparatus operated at a high gain for lasing.
Figure 6B:
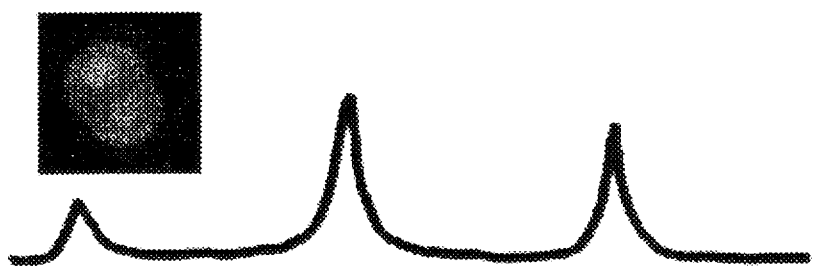
Figure 6C:
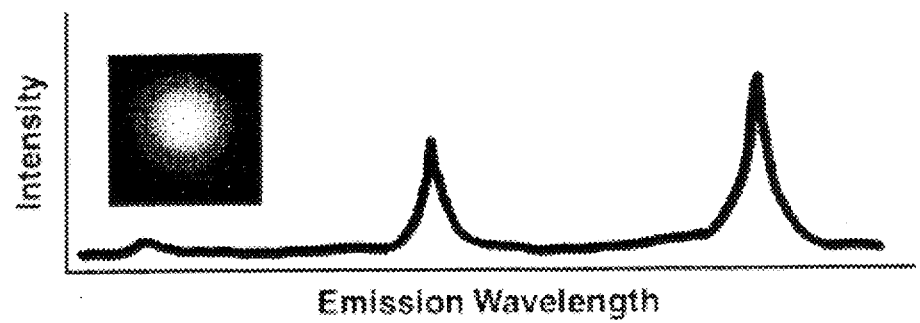

FIG. 6 shows the emission spectra (recorded with the spectrometer 38) and lasing mode images (recorded with a CCD camera 36) for three normal human red blood cells of different sizes as measured with the apparatus 10 with a femtosecond pump laser 26. The cell diameters are about 7.5 μm, 5.7 μm, and 5.0 μm, for FIGS. 6a, 6b, and 6c, respectively. In each case in FIG. 6, the spectra and images comprise a plurality of different transverse modes lasing simultaneously. The emission spectra in FIG. 6 have been recorded on a logarithmic intensity scale (i.e. the intensity scale spans three orders of magnitude from the highest intensity peaks in FIG. 6 to the lowest background signal between the peaks) to enhance observation and measurement of the weaker modes. No absolute wavelength scale is provided in FIG. 6 (although a relative wavelength shift scale is provided) since the different cells were examined at different positions in the analysis region 20, resulting in slightly different cavity lengths, L, between the reflecting mirrors and therefore different absolute wavelengths, $\lambda_{lmn}$, for the longitudinal cavity mode. Only the relative positions of the peaks in FIG. 6 appear to be correlated with properties of the cells. The spectra in FIG. 6 are recorded with the longest wavelength to the right, and a 5 nm-wide wavelength marker is provided for calibrating the wavelength separation between the transverse lasing modes in any of the emission spectra.

In FIGS. 6a, 6b and 6c, the positions of the lasing peaks in the emission spectra are substantially insensitive to the intensity of the pump laser 26 over a wide range, indicating that the cell geometry is primarily responsible for the spectral distribution of the lasing modes in the laser 12. In FIG. 6c, the emission spectrum of a small 5.0-μm-diameter cell shows a dominant peak corresponding to the $TEM_{00}$ lasing mode, and a second weaker peak corresponding to the $TEM_{10}$ mode. The wavelength separation of the two peaks in the emission spectrum of FIG. 6c is relatively wide (about 5.5 nm) due to the small size of this particular red blood cell. The inset image in FIG. 6c appears as a circular (i.e. Gaussian) disk, consistent with the mode distribution of the emission spectrum (i.e. a dominant $TEM_{10}$ lasing mode). This can indicate that the smaller blood cell in FIG. 6c has less biconcavity, therefore favoring lasing in the fundamental $TEM_{00}$ mode.

FIG. 6b shows similar data for a 5.7-μm-diameter normal human red blood cell. For this cell, the $TEM_{10}$ mode (the central peak in the spectrum of FIG. 6b) is dominant in the emission spectrum, with a less intense TEM$_{00}$ lasing mode, and a very weak TEM$_{20}$ lasing mode. The wavelength separation between the TEM$_{00}$ and TEM$_{10}$ lasing modes in FIG. 6b is reduced to about 4.6 nm, consistent with the larger size of this cell. The dominant TEM$_{10}$ mode is also evident in the inset image in FIG. 6b, indicating that this cell has more biconcavity than the cell of FIG. 6c.

FIG. 6a shows yet more data for another red blood cell having a larger diameter of 7.5 µm. The emission spectrum for this cell is more complicated, showing seven transverse lasing modes. The dominant lasing mode as determined by lowering the pump power from the pump laser 26 is the TEM$_{10}$ mode. In FIG. 6a, the higher-order transverse modes have peak emission intensities that for the most part decrease with increasing mode order (and to shorter lasing wavelengths). The wavelength separation between these transverse modes is much smaller (only about 1–2 nm) due to the larger size of this cell. The wavelength separation between the lowest-order modes in FIG. 6a is in general agreement with the calculated mode positions in FIG. 5. However, the wavelength separation between the three highest-order modes (i.e. the three leftmost peaks in the emission spectrum of FIG. 6a) is much less than predicted, indicating that some of the electric field intensity for these modes can be outside the cell boundary.

In FIG. 7, the wavelength separation between the TEM$_{00}$ and TEM$_{10}$ lasing modes is plotted against the cell diameter as measured visually through a microscope for different types of biological cells and for dielectric particles in the form of polystyrene spheres. From these measurements, it can be seen that the wavelength separation increases from less than 1 nm for the largest white blood cells to about 5 nm for the smallest yeast and red blood cells. The biological cell data are in good agreement with the solid-line fit having a slope B/d$^2$ where B is a constant. This calculated curve reflects the above size dependence in the equation for $\Delta\lambda$ from two-dimensional mode theory which is appropriate to the flattened shape of biological cells.

By way of contrast, the data for the polystyrene spheres in FIG. 7 shows a different mode-spacing dependence that is best fitted by three-dimensional mode theory appropriate for spherically-shaped particles. In this case, the calculated solid-line fit has a slope of A/d, where A is another constant. Thus, the apparatus 10 of the present invention can be used to analyze both biological cells and dielectric particles according to both shape and size as shown in FIG. 7.

Figure 8A:
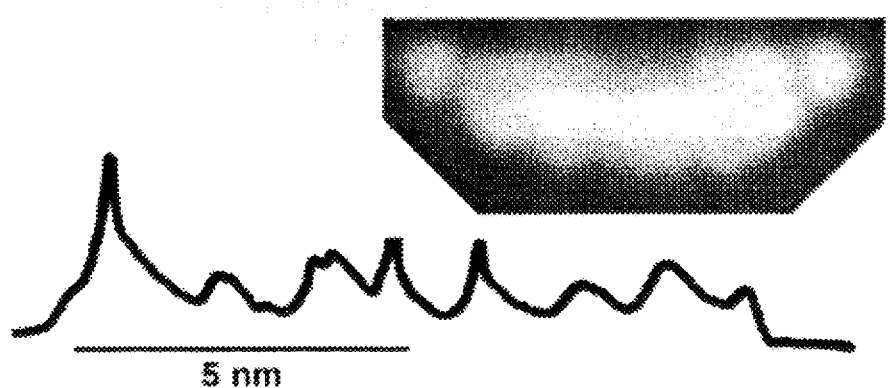
FIGS. 8a, 8b, and 8c show emission spectra and transverse mode profiles generated by the apparatus of the present invention for different sizes of abnormal human red blood cells (i.e. sickle cells) with the apparatus operated at a high gain for lasing.
Figure 8B:
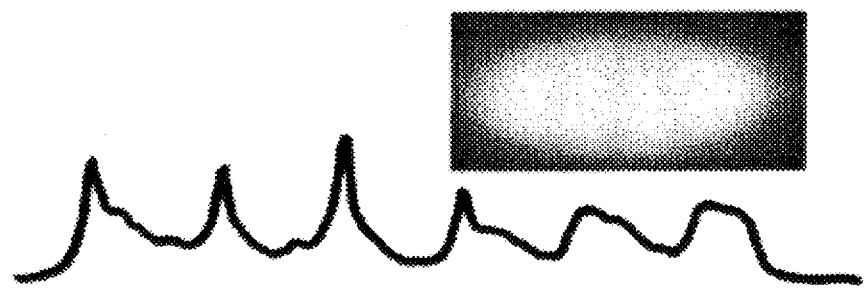
Figure 8C:
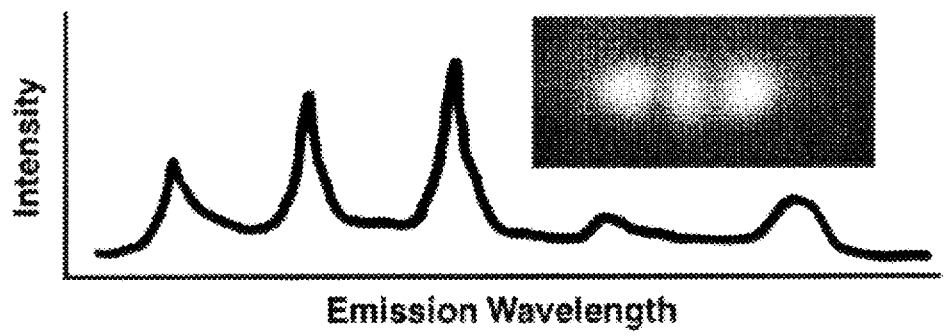

FIG. 8 shows measurements with the apparatus 10 for sickled red blood cells, one of the best understood of molecular diseases. In these abnormal cells, the hemoglobin molecule (HbS) has one amino acid substitution in the β globulin chain which causes the HbS protein to partially crystallize within the cell. With both solid and liquid phases present, the cell acquires the characteristic shape of a sickle, having a long, thin shape that is distinctly different from normal red blood cells. Whole blood from a patient with sickle cell anemia (HbSS) was drawn and diluted in an isotonic media (i.e. carrier fluid) and tested in the apparatus 10 of the present invention under high gain conditions in a manner to that described heretofore for FIG. 6. The sickle shape of these abnormal red blood cells results in transverse lasing modes that are characterized by nodes along the long and short axes of the sickle cell as shown in FIG. 8 for three different sickle cells of lengths from about 8.2 µm to about 11.6 µm. In FIG. 8, each of the images recorded with the analysis means 24 for the cavity 12 lasing shows the linear geometry of the sickle cells, and a number of nodes along one or more axes of the sickle cells. The number of nodes in the lasing light beam 22 increases from two for an 8.2-µm-long cell in FIG. 8c to three for a 9.0-µm-long cell in FIG. 8b, and to seven (six nodes in the vertical direction and one node in the horizontal direction) for the 11.6-µm-long cell in FIG. 8a. The image of FIG. 8c indicates that the lowest-order transverse lasing modes TEM$_{11}$ and TEM$_{21}$ expected for a cell of this shape are not present to any significant extent. This is confirmed from the emission spectra in FIG. 8 which show very broad and weak peaks at the longest wavelengths (to the right in FIG. 8c) indicating amplified spontaneous emission but no lasing at the wavelengths of these lowest-order modes. Instead, the two nodes (i.e. the two dark vertical lines) in the image of FIG. 8c and the location of the strong emission peak in the spectrum both indicate that the dominant lasing mode for this small-size sickle cell is the TEM$_{31}$ mode. (Calculated emission wavelengths and transverse mode profiles for sickle cells are disclosed in the aforementioned article by P. L. Gourley et al.)

In FIG. 8b, the lasing emission spectrum shows three broad, weak peaks at long wavelengths and three stronger and narrower peaks at shorter wavelengths. The weak peaks correspond to the TEM$_{11}$, TEM$_{21}$, and TEM$_{31}$ modes (to shorter wavelengths, respectively) which are either not lasing, or only very weakly lasing. The dominant lasing peak in the spectrum of FIG. 8b is the TEM$_{41}$ mode (the fourth peak from the right) which corresponds to a transverse mode profile having three vertical nodes as in the image of FIG. 8b.

In FIG. 8a, many closely spaced peaks are present in the lasing emission spectrum due to the large size of this sickle cell (11.6 µm long) thereby complicating the interpretation of the emission spectrum. In this spectrum, the peaks are not as uniformly spaced as in FIGS. 8b and 8c, and the distribution of the lasing modes is less well defined. One peak on the extreme left side of the spectrum is dominant, corresponding to the TEM$_{71}$ lasing mode. This transverse mode has six vertical nodes consistent with the image in FIG. 8a. Two weaker lasing modes are also present in the spectrum of FIG. 8a, with the remaining broad, weak peaks being the result of amplified spontaneous emission, but not lasing.

The images and spectra for sickle cells as measured by the apparatus 10 and shown in FIG. 8 are markedly different from the measurements for normal human red blood cells as shown in FIG. 6, thus showing the utility of the apparatus of the present invention for distinguishing between cell types or variants (i.e. between normal and abnormal or diseased cells).

White blood cells are much more complex than red blood cells. White blood cells are larger, vary in shape, and contain a nucleus and other smaller organelles within the cytoplasm. In addition there are several different types of white blood cells classed as polymorphonuclear leukocytes (including polymorphonuclear neutrophils, polymorphonuclear eosinophils, and polymorphonuclear basophils), lymphocytes, and monocytes. This complexity leads to lasing images and spectrum as measured by the apparatus 10 that are rich in structure. Whereas, an entire red blood cell can support lasing, a white blood cell generally only supports lasing in the condensed matter of the nucleus or in the peripheral region outside the nucleus bounded by the cell membrane. In addition, the nucleolus and some larger complexes outside the nucleus can also support lasing. Lasing modes in two common types of white blood cells are described hereinafter.

A first type of white blood cell, polymorphonuclear leukocytes (about 15 µm diameter) comprise a condensed nucleus inside the cell segmented into several irregular lobes (of about 3–5 μm size); small complexes (with dimensions of about 10–100 nm) including mitochondria, golgi bodies, and endoplasmic reticula; and granules (with dimensions of about 200–500 μm) inside a membrane with tiny finger-like projections therefrom (about 100–200 nm long). Optically, all of these structures are substantially transparent to infrared light. The condensed nucleus has convex surfaces and a higher refractive index than surrounding cytoplasm. Some scattering loss can occur from the granules and membrane fingers, but this is not sufficient to prevent the generation of lasing when the cells are in the analysis region 20 of the laser 12 in the apparatus 10.

With the apparatus of the present invention, images of polymorphonuclear neutrophils (a particular type of a polymorphonuclear leukocyte) from whole blood can be obtained with the cavity 12 either operated below or above a threshold for lasing. Below the lasing threshold, the periphery of the cells in an analysis image appears bright (as a sheath that is a few microns thick) compared to the cytoplasm and the external plasma. The bright sheath is likely due to light scattering from the fingered membrane surface of the cell and/or a cytoskeletal network forming the plasma membrane. Within the white blood cell are light and dark regions with low contrast so that the nucleus is not visibly apparent.

As the power in the pump laser beam 28 is increased, amplified spontaneous emission in the cavity 12 begins to build up, increasing the image contrast of the white blood cell and making the nucleus in the cell appear brighter than the light scattered at the membrane. As the power in the pump laser beam 28 is further increased, the cell nucleus begins to support lasing, with the lasing emission at the positions of the cell nucleus being many orders of magnitude brighter than the surrounding spontaneously emitted and scattered light from other parts of the cell. Lasing in multiple transverse modes is typical for white blood cells, even under low gain conditions where the gain bandwidth of the cavity 12 is reduced.

Figure 9:
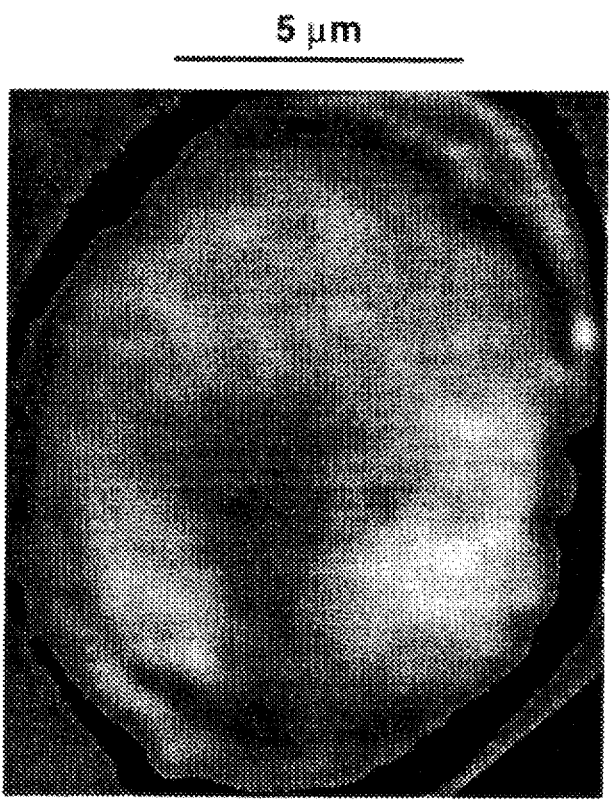
FIG. 9 shows a confocal laser scanning reflected light image of a normal human lymphocyte cell.

With the apparatus 10, a second type of white blood cells, lymphocytes, can also be analyzed with images and spectra generated and recorded to quantify protein/nucleic acid concentrations, and states of activation and proliferation. Lymphocytes are about 10 μm in diameter with a large nucleus that nearly fills the entire cell. FIG. 9 shows a laser scanning confocal micrograph image of a lymphocyte dried in air and placed on a dielectric mirror. In FIG. 9, the large nucleus of the lymphocyte is visible as an oval shape substantially filling the image shown.

Figures 10A, 10B, 10C:
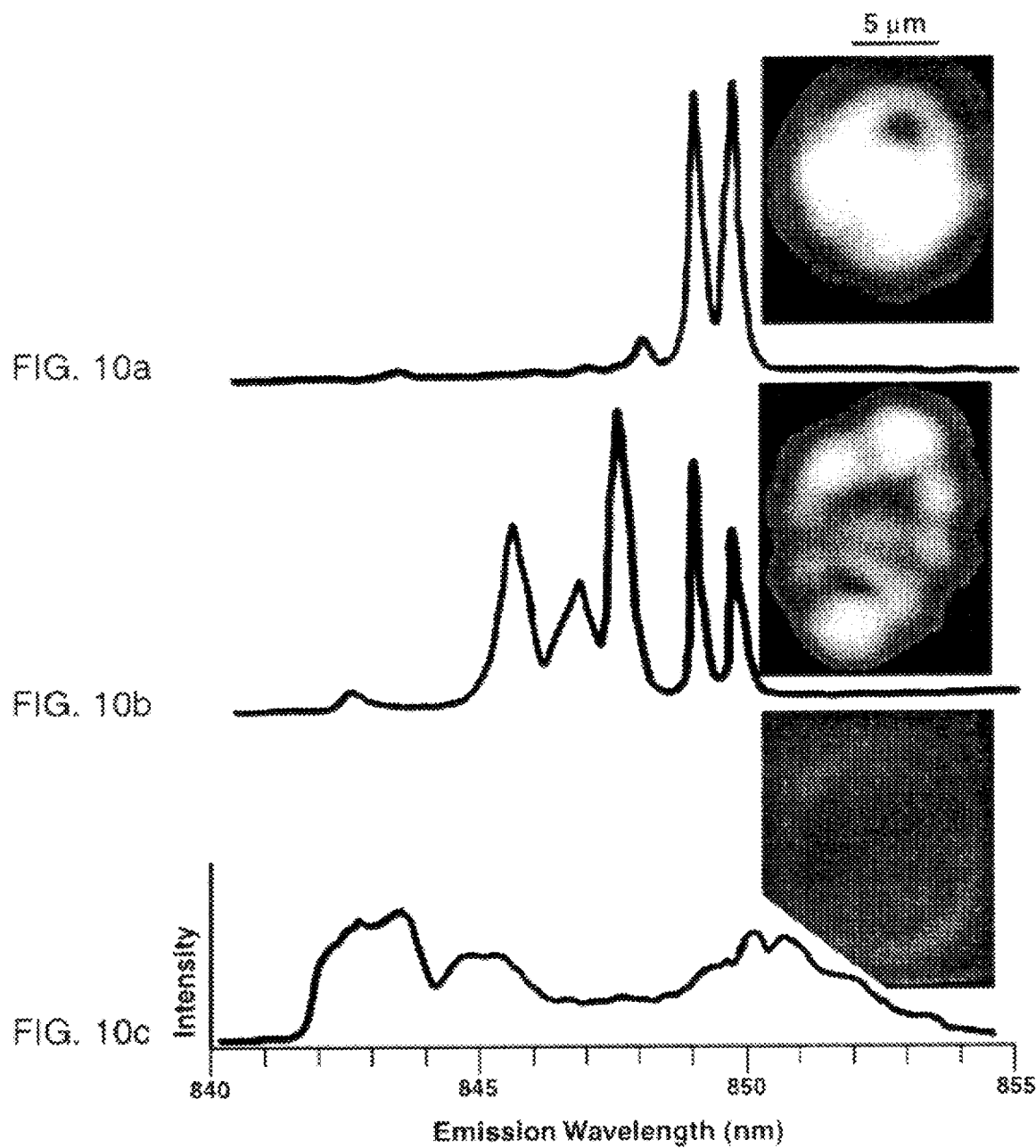
FIGS. 10a, 10b, and 10c show emission spectra and transverse mode profiles generated by the apparatus of the present invention for the normal human lymphocyte cell of FIG. 9 with the apparatus operated at a low gain.

FIGS. 10a–10c show measurements for this same lymphocyte made with the apparatus of the present invention after placing the lymphocyte within the analysis region 20 in the cavity 12. In FIG. 10c, with the cavity 12 operating below a threshold for lasing, an outer membrane of the lymphocyte is highlighted and the emission spectrum shows two broad peaks centered at wavelengths near 843 and 851 nm, respectively.

FIGS. 10a and 10b show the cavity 12 operated above threshold, with the focused pump laser beam being concentric and eccentric with the lymphocyte, respectively. In FIG. 10a, the large nucleus supports lasing in a plurality of transverse modes with peaks in the emission spectrum appearing at wavelengths near 848, 849, and 850 nm. All the transverse lasing modes in FIG. 10a are confined to the nucleus, and reveal subtle variations not apparent in the confocal image of FIG. 9.

The wavelength separation between the transverse modes in the emission spectrum is small (about 1 nm) due to the large size of the lymphocyte. Thus, the apparatus 10 is capable of measuring cell sizes as discussed heretofore with reference to FIG. 7. This ability to measure cell sizes can be advantageous for analyzing cancerous cells that exhibit changes in sizes as compared to normal cells.

In FIG. 10b, eccentric optical pumping of the gain medium 18 results in lasing in a number of filaments substantially around the periphery of the lymphocyte, with the center of the nucleus being relatively dark. Under these conditions, the lasing modes are localized closer to the outer surface of the lymphocyte, and are more sensitive to surface conditions of the cell and its outer membrane. The emission spectrum of FIG. 10b is also distinctly different from that of FIG. 10a, showing a different distribution and number of peaks, with new peaks occurring in the wavelength range between 845 and 848 nm. Thus FIG. 10 shows that the apparatus 10 can be used to analyze the nucleus and cell membrane in a lymphocyte and measure microscopic and spectroscopic differences thereof.

In addition to the measurements described heretofore, the apparatus 10 of the present invention can also be used to analyze other types of cells including blood platelets. Blood platelets can be in the shape of small disks with a diameter of about 4 μm or less. The lasing mode for a platelet within the analysis region 20 of the cavity 12 generally appears circular (i.e. Gaussian), indicating lasing in a $TEM_{00}$ mode; and the emission spectrum shows a single sharp peak corresponding to lasing in only one transverse mode.

The apparatus 10 of the present invention can also be used below a threshold for lasing in the cavity 12 to measure a spontaneous emission spectrum for analysis of one or more cells or particles 100. In this mode of operation, all of the modes of the cavity 12 can be observed simultaneously. Since the spontaneous emission is generally relatively weak, a dominant longitudinal mode of the cavity 12 is also generally present in the emission spectrum. The location of this dominant longitudinal mode in the emission spectrum provides a convenient reference for measuring wavelength shifts of each transverse mode in the emission spectrum due to one or more cells or particles 100 in the analysis region 20 of the cavity 12. These wavelength shifts can be used to calculate the refractive index of one or more cells or particles 100 relative to the surrounding carrier fluid 102 in the analysis region 20. By separately determining the refractive index of the carrier fluid 102 (e.g. by refractometry), absolute values of the refractive indices of the cells or particles 100 can be determined. Additionally, a measurement of the wavelength separation, $\Delta\lambda$, of the transverse modes can be used to quantify the size and shape of the cells or particles as described heretofore and shown in FIG. 7.

Figure 11A:
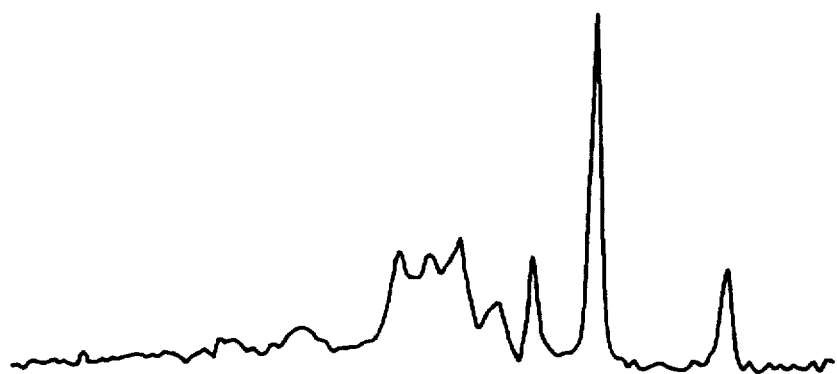
FIG. 11a shows a spontaneous emission spectrum recorded with the apparatus of the present invention with de-ionized water as the carrier fluid in the analysis region, but without any cells or particles present.

FIG. 11a shows a spontaneous emission spectrum recorded with the apparatus 10 of the present invention with de-ionized water as the carrier fluid 102 in the analysis region 20, but without any cells or particles 100 present. The dominant longitudinal mode in FIG. 11a occurs at a wavelength of about 830 nanometers, and is surrounded by a pair of weaker cavity modes at about 820 and 860 nanometers, respectively.

Figure 11B:
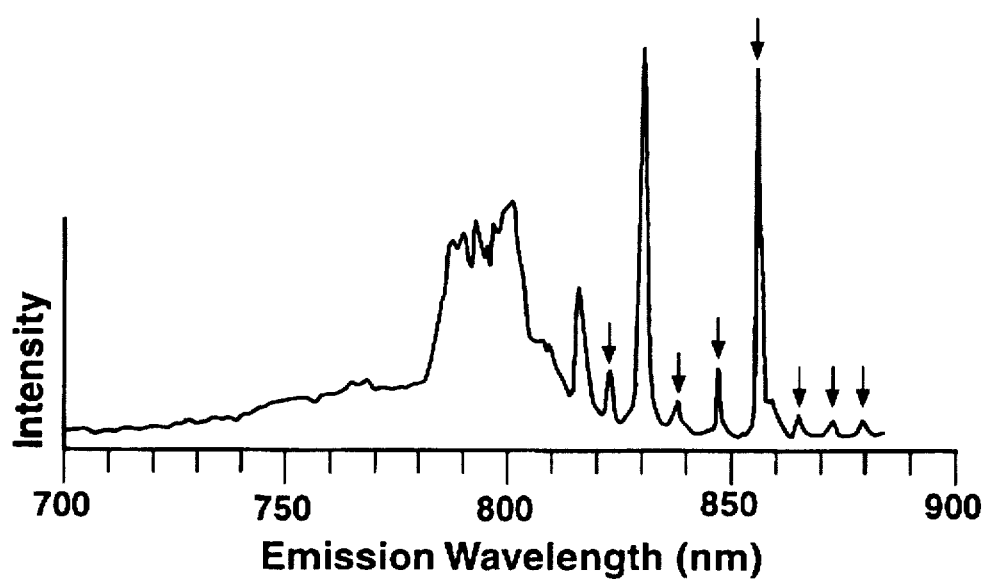
FIG. 11b shows the alteration of the spontaneous emission spectrum of FIG. 11a caused by a single 6-micron spherical particle located within the analysis region.

FIG. 11b shows the alteration of the spontaneous emission spectrum of FIG. 11a and the appearance of a number of transverse modes (indicated by the vertical arrows in FIG. 11b) due to the presence of a single 6-micron polystyrene microsphere 100(n=1.59) in the de-ionized water in the analysis region 20. The number of these transverse modes, their wavelength spacings and wavelength shifts $\Delta\lambda$, and their intensity distribution and integrated intensity provide information for quantifying the size, shape and refractive index of one or more cells or particles 100 being analyzed with the apparatus 10.

Figure 12A:
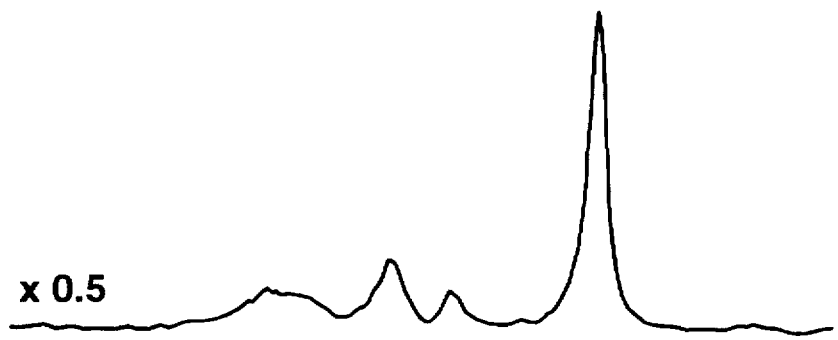
FIG. 12a shows an emission spectrum for an unloaded cavity with only de-ionized water present in the analysis region of the cavity.
Figure 12B:
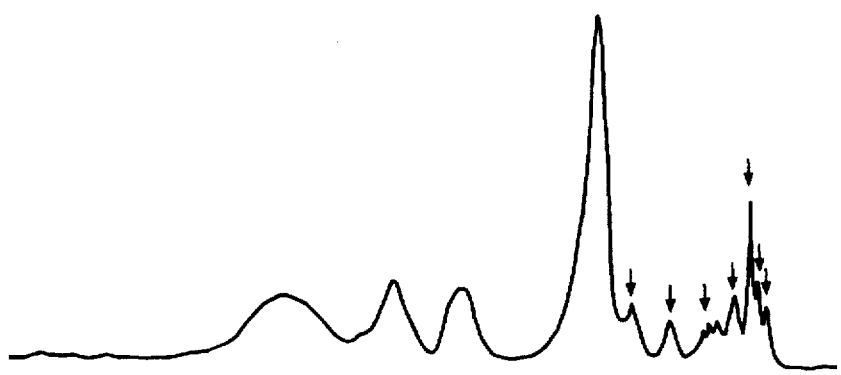
FIG. 12b shows a spontaneous emission spectrum obtained with the cavity loaded with a red blood cell surrounded by de-ionized water as the carrier fluid in the analysis region of the cavity.
Figure 12C:
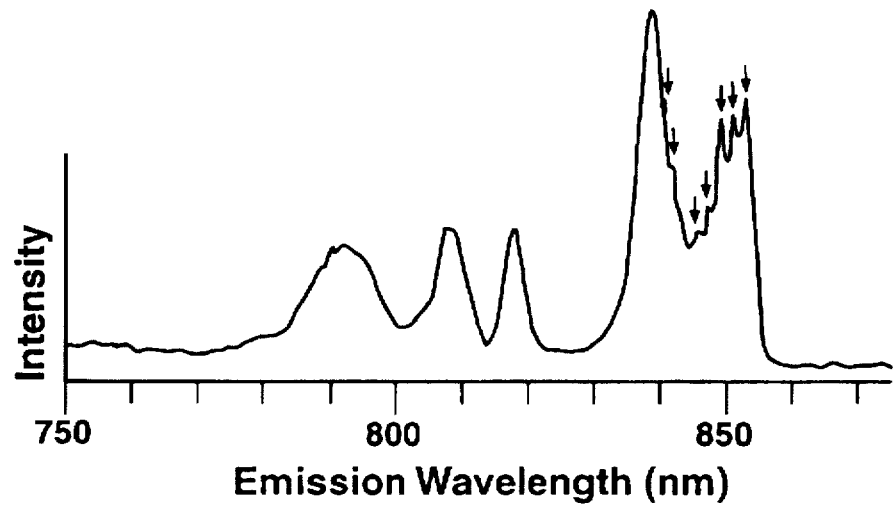
FIG. 12c shows another spontaneous emission spectrum obtained with a white blood cell in de-ionized water in the analysis region of the cavity.

FIGS. 12a–12c show similar spontaneous emission spectra for biological cells 100 being analyzed by the apparatus 10. FIG. 12a shows an emission spectrum for the unloaded cavity with only de-ionized water present in the analysis region 20 as a carrier fluid 102. Three longitudinal cavity modes are present in FIG. 12a in the wavelength range 800–850 nanometers. FIG. 12b shows a spontaneous emission spectrum obtained with the cavity 12 loaded with a red blood cell surrounded by de-ionized water as the carrier fluid 102 in the analysis region 20. The presence of the red blood cell in the cavity 12 alters the emission spectrum by producing a number of transverse mode peaks indicated by the vertical arrows in FIG. 12b, with the transverse modes providing information about the size and other characteristics of the red blood cell. FIG. 12c shows another spontaneous emission spectrum that is obtained when the cavity 12 contains a white blood cell in de-ionized water within the analysis region 20. The larger size of the white blood cell results in a closer spacing of the transverse modes (indicated by the vertical arrows) compared with the red blood cell of FIG. 12b (see also FIG. 7).

Figure 13:
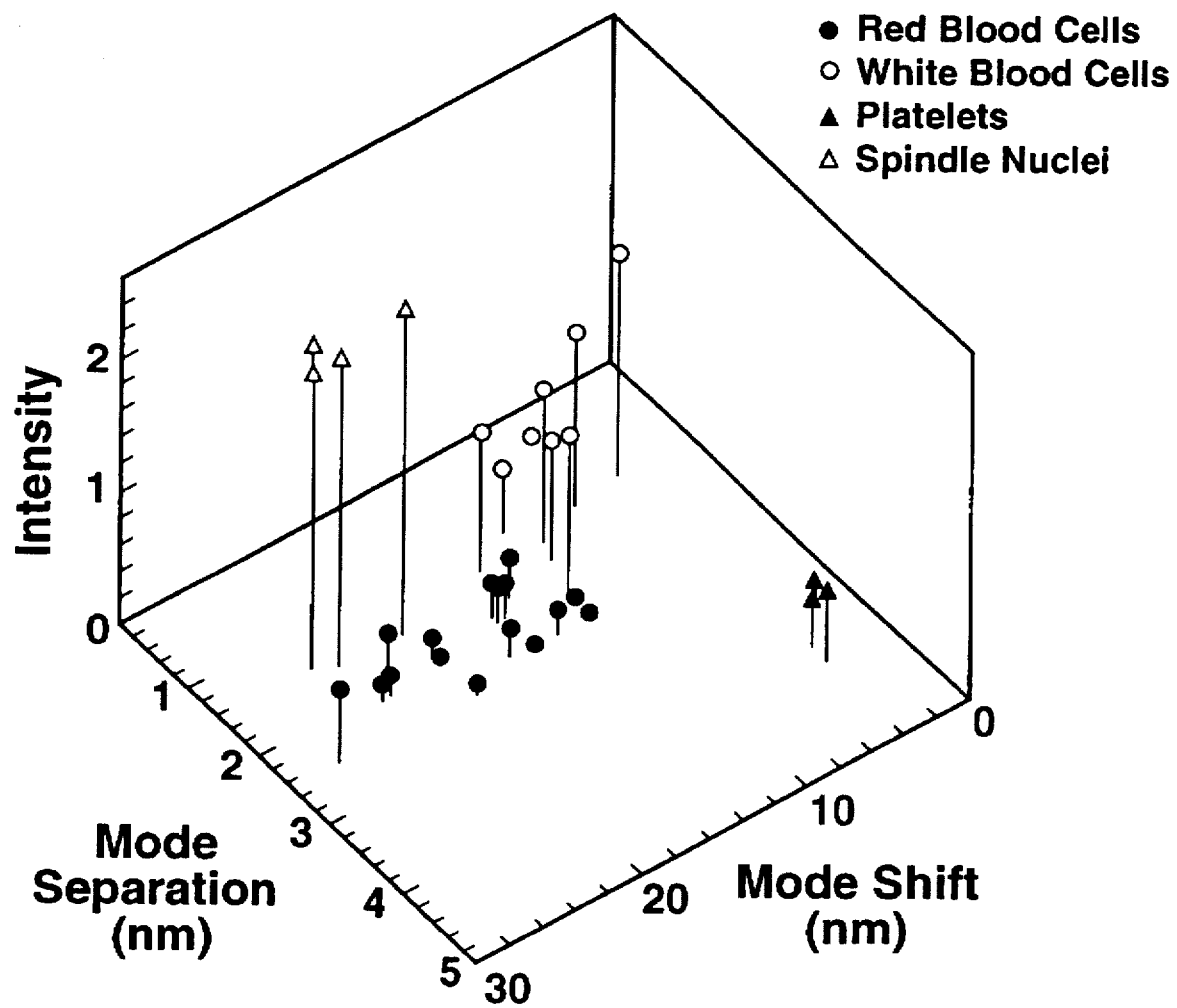
FIG. 13 shows a three-dimensional plot showing that different types of biological cells can be grouped and distinguished using information derived from the cells with the apparatus of the present invention.

A sample containing different types and sizes of biological cells or dielectric particles 100 can be analyzed with the apparatus 10 of the present invention by mapping the information derived from the analysis means 24 in a multi-dimensional coordinate space. For example, FIG. 13 shows a method for classifying biological cells that maps data derived from the analysis means 24 for a sample containing a plurality of biological cells 100 of four different types. In FIG. 13, the data is mapped into a three-dimensional coordinate space, with the coordinates corresponding to the transverse mode spacing (proportional to a diameter of each cell), the transverse mode shift $\Delta\lambda$ (proportional to a refractive index, n, of each cell), and the integrated intensity of all the transverse modes generated by each cell normalized to the intensity of the dominant longitudinal mode (proportional to a volume of each cell). In FIG. 13, the different types of cells, including red and white blood cells, platelets and spindle nuclei from a placental tumor are readily identified and distinguished due to the clustering of the cells of each type into distinct groupings within the three-dimensional coordinate space. This method allows a large sample population of different cells to be analyzed solely on the basis of information derived from the apparatus 10 of the present invention, without any need for visual imaging or computer image processing of the cells. This method of the present invention can be used to automate cell identification and sorting based on computer algorithms which process one-dimensional information (e.g. spectral data) recovered from the light beam 22 by the analysis means 24. Computer processing of one-dimensional information is advantageous since it can be done much faster than processing of two-dimensional information derived from cell images. Thus, the present invention can be used to provide an improved rate for cell or particle analysis, allowing large populations of cells or particles 100 to be analyzed in a short period of time (at a potential analysis rate of up to about $10^5$–$10^6$ cells or particles per second).

Figure 14:
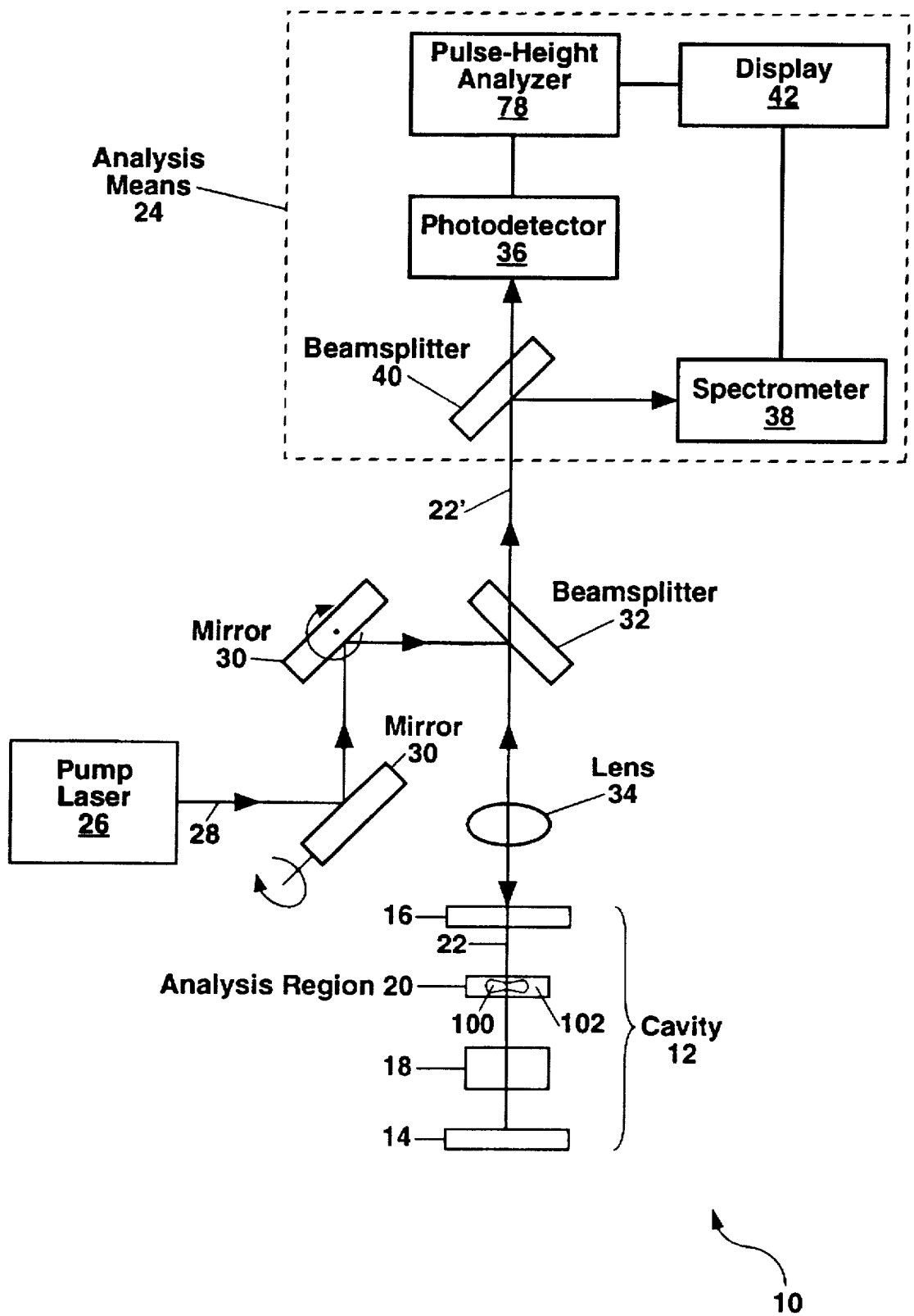
FIG. 14 shows a schematic diagram of a second embodiment of the apparatus in the form of a scanning cytometer for analyzing a plurality of biological cells or dielectric particles.

FIG. 14 shows a schematic diagram of a second embodiment of the apparatus 10 in the form of a cytometer for analyzing a plurality of biological cells or dielectric particles. In FIG. 14, the second embodiment of the present invention is similar to the first embodiment of FIG. 1, but the analysis means 24 further includes a pulse-height analyzer 78 for processing pulses of lasing light that are emitted from the cavity 12 in response to a pump laser beam 28 being raster scanned across a plurality of cells or particles 100 located within the analysis region 20 of the cavity. The second embodiment of the apparatus 10 in FIG. 14 can be used as a laser-scanning cytometer to rapidly probe and analyze large populations of biological cells or dielectric particles 100 located within the analysis region 20.

The analysis means 24 can be used to analyze the portion 22' of the light beam 22 and to derive therefrom images and spectra containing information about one or more cells or particles 100 placed within the analysis region 20 of the apparatus 10. Additionally, the pulse-height analyzer 78 in analysis means 24 can be used to obtain information about the size and uniformity of a plurality of cells or particles 100 within the analysis region 20.

Figure 15:
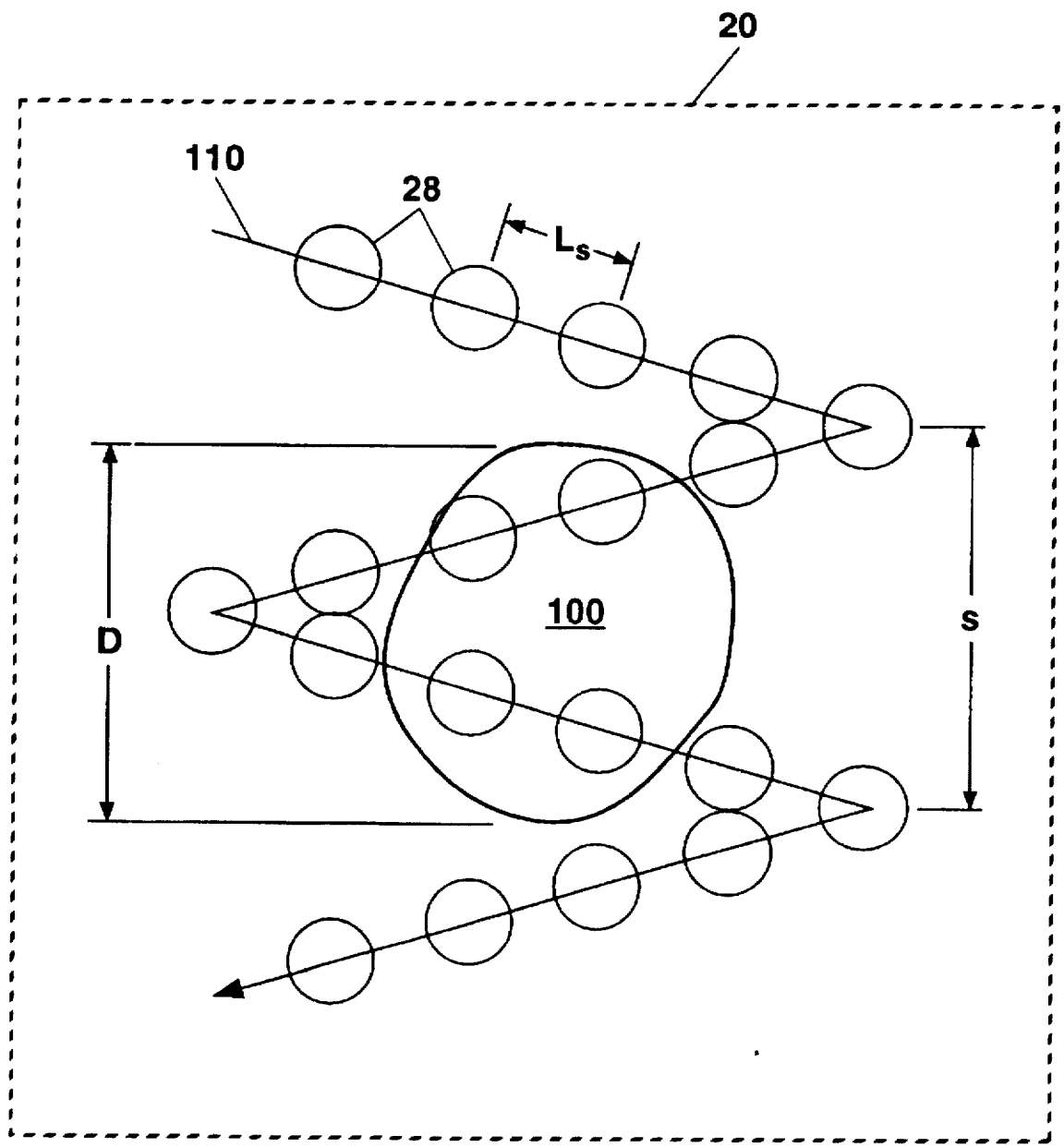
FIG. 15 shows a schematic diagram for illustrating operation of the second embodiment of the apparatus in FIG. 14.

Operation of the apparatus 10 of FIG. 14 as a scanning cytometer can be understood with reference to FIG. 15 which shows schematically a pump laser beam 28 focused to a spot size smaller than the cell or particles 100 to be analyzed, with the pump laser 26 being operated in a pulsed mode and with the pump beam 28 being raster scanned along a path 110 that intercepts a particular cell or particle 100 in the analysis region 20. In FIG. 15, the pump laser 26 is operated to provide a continuous train of short pulses at a rate of up to several MHz (e.g. with a cavity-dumped argon ion or krypton ion laser 26), with each pulse being generally about 10 nanoseconds or less in duration and separated in space by a distance, $L_s$, which depends on a raster scanning rate and a pulse-repetition rate of the pump laser 26. A line spacing, s, for the raster scan can be selected depending upon a size, D, of a particular type of cells or particles 100 to be analyzed. For simply counting the number of cells or particles 100, a Nyquist sampling condition with s≈D can be used so that each cell or particle 100 is sampled at least twice by the focused pump beam 28. Additionally, the distance, $L_s$, between adjacent pulses of light in the focused pump beam 28 can be set at $L_s$≈D/2 to satisfy the Nyquist sampling condition. As the focused pump beam 28 is scanned across each cell or particle 100 in the analysis region 20, about 2–20 pulses of light can be generated by the resonant optical cavity 12 depending upon the pulse-repetition rate and a raster scan rate. These pulses of light form the light beam 22 which is transmitted to the photodetector 36 for detection and analysis by the pulse-height analyzer 78. The photodetector 36, in this mode of operation of the apparatus 10, can be either a p-i-n or an avalanche photodetector with a response time about that of the pulse duration of the pump laser 26 or less (e.g. ≦10 nanoseconds response time). A response time of the resonant optical cavity 12 is about 10 picoseconds so that the generated light beam 22 will follow the pump laser pulse.

By integrating the number of pulses of light produced when the focused laser beam 28 is scanned across each cell or particle 100, the pulse-height analyzer 78 can be used to determine the cell or particle size. Thus, a pulse-height distribution or spectrum produced with the pulse-height analyzer 78 can be used to analyze and display a size distribution of cells or particles 100.

Figure 16A:
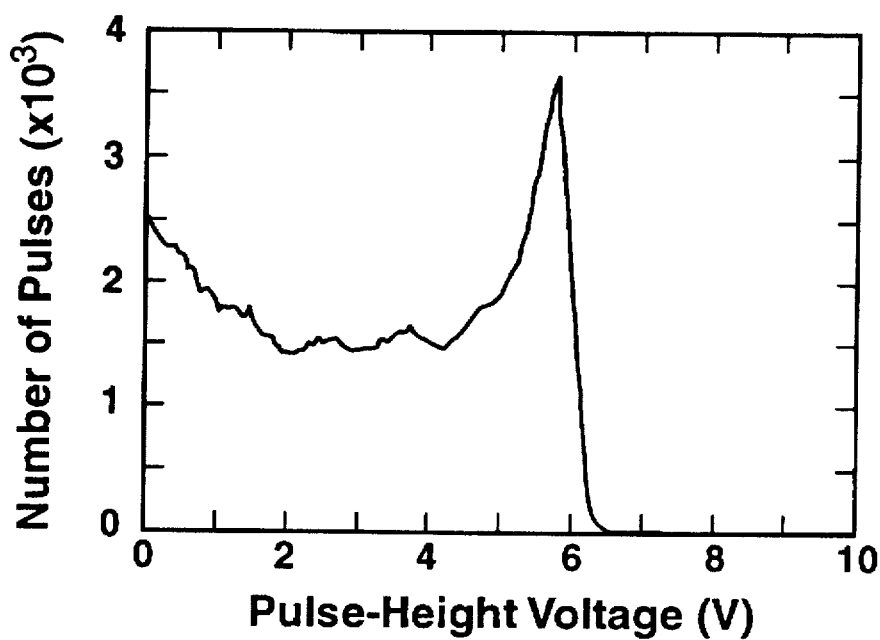
FIG. 16a shows a pulse-height distribution for a single 6-micron spherical particle obtained with the apparatus of FIG. 14.

FIG. 16a shows a pulse-height distribution for a single 6-micron spherical particle 100 obtained with the apparatus 10 of FIG. 14. The pulse-height distribution in FIG. 16a was obtained by raster scanning the focused pump beam 28 with the raster scan line spacing, s, set to be much smaller than the 6-micron particle size. During successive raster scans, the overlap of the focused pump beam 28 with the particle 100 produces a light beam 22 having a Gaussian pulse-train envelope. This Gaussian pulse-train envelope results in a pulse-height distribution having a saddle-like shape with the highest probability for a given pulse-height voltage being located near the minimum and maximum values of pulse-height voltages as shown in FIG. 16a due to the raster scanned pump beam 28 either missing the particle completely or scanning directly over the particle. (The signal between the peaks in FIG. 16a is due to an incomplete overlap between the raster-scanned pump beam 28 and the particle 100.) Thus, the pulse-height voltage can provide a measure of the size of each particle 100 while the number of pulses counted in the pulse-height analyzer 78 can be related to the number of particles of a given size (or in the case of the single particle in FIG. 16a, to the number of times the particle is raster scanned).

If many randomly distributed similarly sized and shaped cells or particles 100 are analyzed with the apparatus 10 of FIG. 14 by raster scanning the focused pump beam 28 with s≈D, then a pulse-height distribution having a shape similar to that of FIG. 16a will generally be obtained. However, in the unlikely event that the locations of the cells or particles 100 were to be correlated with the path 110 of the raster scanned pump beam 28, the pulse-height distribution could be enhanced or suppressed at certain values of pulse-height voltage.

In the most general case, the cells or particles 100 to be analyzed will normally be randomly distributed with different sizes or shapes. In this case, the pulse-height distribution obtained with the apparatus 10 of FIG. 14 will have multiple peaks that can provide information about the distribution of sizes or shapes of the cells or particles 100 being analyzed. Larger cells and particles 100 and those cells and particles having low internal light scattering will provide a peak in the pulse-height distribution at a high value of the pulse-height voltage; whereas smaller cells or particles will provide a peak in the spectrum at a lower value of the pulse-height voltage. All of the cells or particles 100 should also produce a peak near the zero value of the pulse-height voltage if the pulse train is Gaussian. Consequently, the pulse-height distribution for a random distribution of differently sized or shaped cells or particles 100 can have a large peak near zero pulse-height voltage, with additional peaks at higher values of the pulse-height voltage. The number of peaks in the pulse-height distribution will depend on the number of distinct cell types or the number of different sized particles being analyzed. A smearing of the pulse-height distribution can also occur when there is a continuous size variation in the cells or particles 100 being analyzed.

Figure 16B:
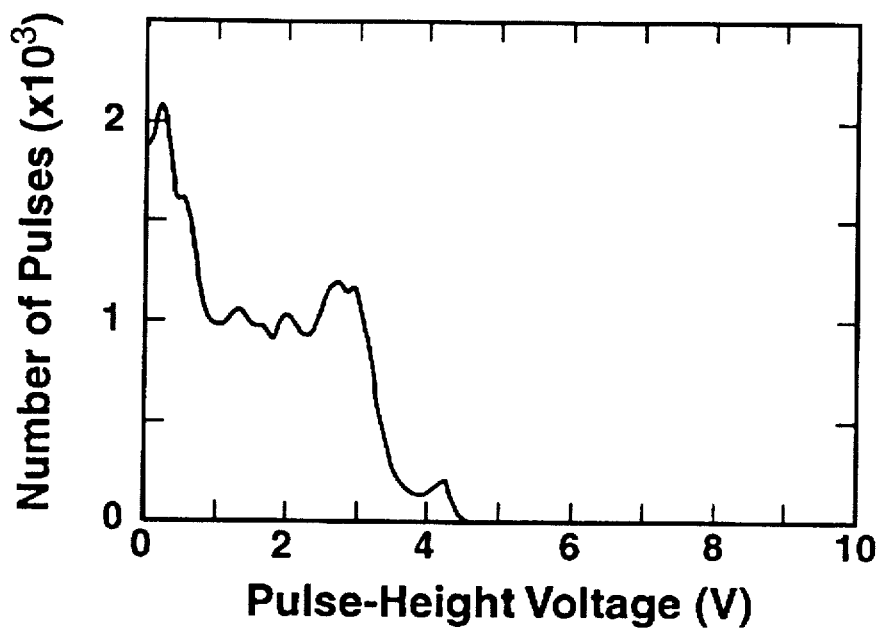
FIG. 16b shows a pulse-height distribution obtained with the apparatus of FIG. 14 for a sample of about one-hundred spherical particles with a distribution of different discrete particle sizes.

FIG. 16b shows a pulse-height distribution obtained with the apparatus 10 of FIG. 14 for a sample of about one-hundred spherical particles with a distribution of different discrete particle sizes. The pulse-height distribution of FIG. 16b shows about seven distinct peaks due to different sizes of the spherical particles 100. In FIG. 16b, the number of pulses recorded for each peak in the pulse-height distribution provides a measure of the relative number of particles of that particular size in the sample being analyzed when normalized to the number of times the particles are raster scanned.

Figure 17A:
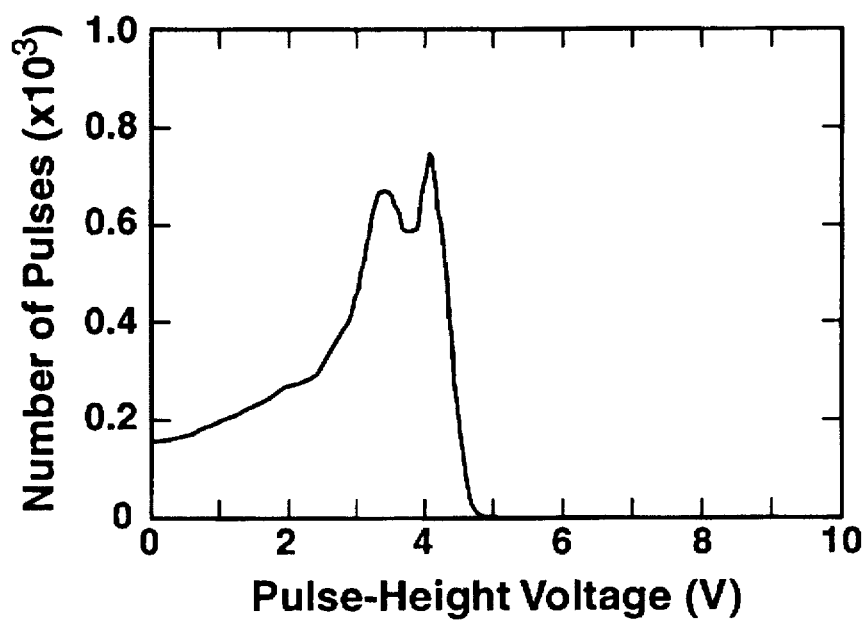
FIG. 17a shows a pulse-height distribution obtained with the apparatus of FIG. 14 for a single normal human red blood cell.
Figure 17B:
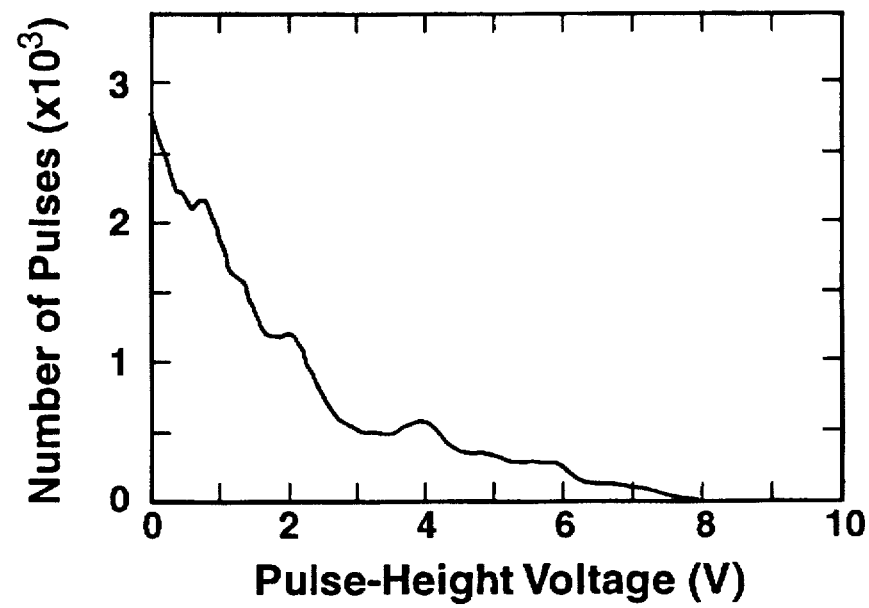
FIG. 17b shows a pulse-height distribution obtained from a sample of about one-hundred normal human red blood cells with the apparatus of FIG. 14.

FIG. 17a shows a pulse-height distribution obtained with the apparatus 10 of FIG. 14 for a single normal human red blood cell. FIG. 17a shows a pulse-height distribution that is double-peaked near the maximum pulse-height voltage with a decreasing intensity (i.e. number of pulses) towards zero pulse-height voltage. The absence of a peak in the spectrum of FIG. 17a at zero pulse-height voltage can be attributed to the shape of the pulse-train envelope which is far from Gaussian. FIG. 17b shows a pulse-height distribution obtained from a sample of about one-hundred normal human red blood cells. The pulse-height distribution of FIG. 17b shows a generally decreasing intensity with increasing pulse-height voltage and several small peaks at selected values of the pulse-height voltage. The pulse-height distribution of FIG. 17b is less distinct than that of FIG. 16b due to the double-peaked nature of the single-cell spectrum of FIG. 17a, and also due to a large variation in sizes of the red blood cells.

FIGS. 18a and 18b show images of the samples of about one-hundred spherical particles and normal human red blood cells, respectively. These images were recorded with the apparatus 10 of the present invention from the light beam 22. As the pump laser beam 28 is raster scanned across the cells or particles 100 in the analysis region 20, substantial light in the beam 22 is generated at the location of each cell or particle 100, with little or no light being generated at locations wherein no cells or particles are present. Thus, an image of the cells or particles 100 being analyzed can be easily and quickly recorded with either a camera, or with a display 42 having inputs from the photodetector 36 and the steering means. This image can also be digitized and stored in a computer.

FIG. 19 shows a fourth example of an apparatus for analyzing cells or particles according to the present invention. In FIG. 19, the resonant optical cavity 12 is a composite cavity comprising a pair of sub-cavities each formed by a pair of adjacent mirrors, with a first sub-cavity containing the semiconductor gain medium 18 and a second sub-cavity containing the analysis region 20. The first and second sub-cavities are formed with an intermediate mirror 80 in common so that the sub-cavities are optically coupled together to form the composite cavity 12.

In the example of FIG. 19, a vertical-cavity surface-emitting semiconductor laser can be formed in part by the first sub-cavity by growing on a semiconductor substrate 50, a lower reflecting mirror 14, a semiconductor gain medium 18 having a p-n or p-i-n junction therein, and the intermediate reflecting mirror 80 (e.g. a distributed Bragg reflector mirror comprising a plurality of alternating one-quarter-wavelength thick layers of high- and low-refractive-index semiconductor materials with a semiconductor doping type opposite that of the lower reflecting mirror 14). Fabrication of the vertical-cavity surface-emitting semiconductor laser can be completed by forming a patterned upper electrode 60 overlying a patterned insulating layer 54 and contacting the intermediate mirror 80 as shown in FIG. 19, and by forming a lower electrode 58 below the semiconductor substrate 50. The vertical-cavity surface-emitting laser can be fabricated for operation at a predetermined wavelength and tested prior to fabrication of the upper reflecting mirror 16 and formation of the analysis region 20.

The upper reflecting mirror 16 can be formed on a transparent substrate 56 as described heretofore in the discussion of FIGS. 3a and 3b, with the upper mirror 16 comprising, for example, a plurality of alternating one-quarter-wavelength thick layers of high- and low-refractive index dielectric materials. The analysis region 20 can be formed by contacting the upper reflecting mirror 16 with the vertical-cavity surface-emitting laser with or without one or more intervening passivation layers 82 provided for protection or biocompatibility.

An effective optical spacing between the intermediate mirror 80 and the upper reflecting mirror 16 can be predetermined taking into account the refractive indices of the carrier fluid 102 and the types of cells or particles 100 to be analyzed. This effective optical spacing of the second sub-cavity can be predetermined so that it is about an integer multiple of an effective optical thickness (i.e. an actual layer thickness multiplied by the index of refraction) of the gain medium 18 to provide for efficient optical coupling between the two sub-cavities. An electrical current flow between the upper and lower electrodes can then be used to activate portion 52 of the gain medium 18 to produce a light beam 22 due to spontaneous emission or lasing action, with the light beam 22 being coupled into the second optical cavity where it interacts with one or more cells or particles 100 therein. The cells or particles 100 act as lenses or optical waveguides increasing the optical confinement of light within the composite cavity 12 and impressing information about the cells or particles 100 onto the light beam 22. This information is recoverable by the analysis means 24 as described heretofore.

Although FIG. 19 shows the fourth example of the present invention as an electrically activated device, it will be understood by those skilled in the art that an optically-pumped device can be similarly formed by omitting the electrodes 58 and 60 and providing a pump laser beam 28 that is coupled into the gain medium 18 either upward through the lower reflecting mirror 14, or downward through the upper reflecting mirror 16.

The matter set forth in the foregoing description and accompanying drawings is offered by way of illustration only and not as a limitation. Other applications and variations of the apparatus and method of the present invention for analyzing cells or particles will become evident to those skilled in the art from practice of the invention. Examples of applications for analyzing biological cells include probing human or animal cells for characterizing immune systems (e.g. for analyzing surface properties of leukocytes); characterizing human or animal genetic disorders (e.g. for analyzing a crystallization of hemoglobin in sickled red blood cells); analyzing and processing cell types (e.g. sorting XX and XY sperm for sex selection or in-vitro fertilization); and analyzing cancerous cells. The actual scope of the invention is intended to be defined in the following claims when viewed in their proper perspective based on the prior art.

What is claimed is:

1. Apparatus for analyzing cells or particles comprising:
   (a) a resonant optical cavity comprising a pair of adjacent mirrors oriented parallel to each other, and further including a semiconductor optical gain medium located between the mirrors and an analysis region located between the mirrors for containing at least one cell or particle to be analyzed; and
   (b) pump means for activating the gain medium to generate spontaneous emission within the resonant optical cavity, with the spontaneous emission having information about the cell or particle encoded thereupon.

2. The apparatus of claim 1 further including analysis means for receiving a portion of the spontaneous emission and recovering the information about the cell or particle.

3. The apparatus of claim 2 wherein the analysis means includes a spectrometer.

4. The apparatus of claim 1 wherein the information is in the form of an optical characteristic of the spontaneous emission selected from the group consisting of an emission spectrum, an optical intensity profile, or a combination thereof.

5. The apparatus of claim 1 wherein the analysis region is located within a flow cell.

6. The apparatus of claim 1 wherein the gain medium further includes a fluorescent stain.

7. The apparatus of claim 1 wherein the spontaneous emission has a wavelength of about 0.2 to 10 microns.

8. The apparatus of claim 1 wherein the resonant optical cavity is formed proximate to a semiconductor substrate.

9. The apparatus of claim 1 wherein the gain medium includes a semiconductor junction.

10. The apparatus of claim 9 wherein the pump means for activating the gain medium is an electrical current applied across the semiconductor junction.

11. The apparatus of claim 1 wherein the pump means for activating the gain medium is a pump laser providing a pump laser beam for activating at least a portion of the gain medium.

12. The apparatus of claim 11 further including steering means for steering the pump laser beam to define a plurality of different activated portions of the gain medium.

13. The apparatus of claim 1 wherein at least one mirror forming the resonant optical cavity is a distributed Bragg reflector mirror.

14. The apparatus of claim 13 wherein the distributed Bragg reflector mirror comprises a plurality of alternating layers of high-refractive-index and low-refractive-index materials.

15. The apparatus of claim 1 wherein the resonant optical cavity comprises, at least in part, a vertical-cavity surface-emitting laser, with the spontaneous emission being generated below a threshold for lasing of the vertical-cavity surface-emitting laser.

16. Apparatus for analyzing cells or particles comprising:
   (a) a resonant optical cavity comprising a pair of optically coupled sub-cavities with the sub-cavities sharing a common mirror, and each sub-cavity having another adjacent mirror spaced at a distance from the common mirror and parallel thereto, one of the sub-cavities including an optical gain medium and the other of the sub-cavities including an analysis region for containing at least one cell or particle to be analyzed;
   (b) pump means for activating the gain medium to generate a light beam within the resonant optical cavity, the light beam having information about the cell or particle encoded thereupon.

17. The apparatus of claim 16 further including analysis means for receiving a portion of the light beam and recovering the information about the cell or particle.

18. The apparatus of claim 17 wherein the analysis means includes at least one analysis element selected from the group consisting of a spectrometer and a pulse-height analyzer.

19. The apparatus of claim 16 wherein the information is in the form of an optical characteristic of the light beam selected from the group consisting of an emission spectrum, an optical intensity profile, or a combination thereof.

20. The apparatus of claim 16 wherein the gain medium includes a semiconductor junction.

21. The apparatus of claim 20 wherein the pump means for activating the gain medium is an electrical current applied across the semiconductor junction.

22. The apparatus of claim 16 wherein the pump means for activating the gain medium is a pump laser providing a pump laser beam for activating at least a portion of the gain medium.

23. The apparatus of claim 22 further including steering means for steering the pump laser beam to define a plurality of different activated portions of the gain medium.

24. The apparatus of claim 16 wherein the resonant optical cavity comprises, at least in part, a vertical-cavity surface-emitting laser.

25. Apparatus for analyzing cells or particles comprising:

(a) a first laser having a resonant optical cavity including a gain medium and an analysis region for containing at least one cell or particle to be analyzed;

(b) a second laser for providing a pump laser beam for activating the gain medium to generate a laser beam within the resonant optical cavity of the first laser, with the laser beam having information about the cell or particle encoded thereupon;

(c) steering means for steering the pump laser beam to activate different portions of the gain medium; and (d) a pulse-height analyzer for analyzing the laser beam and recovering the information about each cell or particle therefrom.

26. The apparatus of claim 25 wherein the first laser is a vertical-cavity surface-emitting laser.

27. The apparatus of claim 25 further including a spectrometer for analyzing the laser beam and recovering additional information about each cell or particle therefrom.

28. A method for analyzing a plurality of cells or particles comprising the steps of:

(a) locating the cells or particles within an analysis region within a resonant optical cavity containing a gain medium;

(b) activating a portion of the gain medium by a pump means, scanning the activated portion across the gain medium, and generating a light beam within the resonant optical cavity at the location of at each cell or particle;

(c) encoding the light beam with information about each cell or particle;

(d) recovering the information about each cell or particle by analyzing the light beam; and (e) plotting the recovered information about each cell or particle in a multi-dimensional coordinate space wherein the recovered information from a particular type of cell or particle is grouped to provide for identification thereof.

* * * * *